United States Patent
Hayashi et al.

US010457982B2

(10) Patent No.: US 10,457,982 B2
(45) Date of Patent: Oct. 29, 2019

(54) METHOD FOR NUCLEIC ACID AMPLIFICATION

(71) Applicant: RIKEN, Saitama (JP)

(72) Inventors: Tetsutaro Hayashi, Saitama (JP); Yohei Sasagawa, Saitama (JP); Itoshi Nikaido, Saitama (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 15/514,931

(22) PCT Filed: Sep. 30, 2015

(86) PCT No.: PCT/JP2015/077745
§ 371 (c)(1),
(2) Date: Jun. 15, 2017

(87) PCT Pub. No.: WO2016/052619
PCT Pub. Date: Apr. 7, 2016

(65) Prior Publication Data
US 2017/0275685 A1 Sep. 28, 2017

(30) Foreign Application Priority Data
Sep. 30, 2014 (JP) ................... 2014-200258

(51) Int. Cl.
| | |
|---|---|
| *C12P 19/34* | (2006.01) |
| *C12Q 1/6853* | (2018.01) |
| *C12N 15/09* | (2006.01) |
| *C12Q 1/6874* | (2018.01) |
| *C12N 9/16* | (2006.01) |
| *C40B 40/06* | (2006.01) |

(52) U.S. Cl.
CPC ........... *C12Q 1/6853* (2013.01); *C12N 15/09* (2013.01); *C12Q 1/6874* (2013.01); *C12N 9/16* (2013.01); *C40B 40/06* (2013.01)

(58) Field of Classification Search
CPC .......... C12N 15/09; C12N 9/16; C40B 40/06; C12Q 1/6853; C12Q 1/6874
USPC ........................................... 435/91.2
See application file for complete search history.

(56) References Cited

U.S. PATENT DOCUMENTS

| | | |
|---|---|---|
| 2005/0084875 A1 | 4/2005 | Coleman et al. |
| 2011/0020878 A1 | 1/2011 | Lanes et al. |
| 2014/0213485 A1* | 7/2014 | Weissman .......... C12N 15/1096 506/26 |

FOREIGN PATENT DOCUMENTS

| | | |
|---|---|---|
| EP | 1707623 A1 | 10/2006 |
| EP | 1736775 A1 | 12/2006 |
| EP | 2666870 A1 | 11/2013 |
| JP | 2014-103867 | 6/2014 |
| JP | 2014103867 | * 6/2014 |

OTHER PUBLICATIONS

Promega product sold since 2012.*
Nilsen et al., PLOS ONE, 5 (4): e10295, 1-9, (Year: 2010).*
Cal et al., EMBO Journal, 17 (23), 7128-7138, (Year: 1998).*
Moreau et al., Nucleic Acids Research, 37 (19), e130, 1-14, (Year: 2009).*
Perales et al., Nucleic Acids Research, 31 (22), 6473-7480, (Year: 2003).*
Mullis, "Specific Enzymatic Amplification of DNA In Vitro: The Polymerase Chain Reflection", Cold Spring Harb Symp Quant Biol, 1986, pp. 263-273.
Walker, "Isothermal in vitro amplification of DNA by a restriction exzyme/DNA polymerase system.", Proc Natl Acad Sci USA, Jan. 1992, vol. 89, pp. 392-396.
Dean, "Comprehensive human genome amplification using multiple displacement amplification", Proc Natl Acad Sci USA, Apr. 16, 2002, vol. 99, No. 8, pp. 5261-5266.
Lizardi, "Mutation detection and single-molecule counting using isothermal rolling-circle amplification", Nat Genet., Jul. 19, 1998, vol. 19, pp. 225-232.
Notomi, "Loop-mediated isothermal amplification of DNA", Nucleic Acids Res., Apr. 15, 2000, vol. 28, No. 12, e63, pp. i-vii.
Mitani, "Rapid SNP diagnostics using asymmetric isothermal amplification and a new mismatch-suppression technology", Nat Methods, Mar. 2007, vol. 4, No. 3, pp. 257-262.
Vincent, "Helicase-dependent isothermal DNA amplification", EMBO rep., Aug. 2004, vol. 5, No. 8, pp. 795-800.
Barany, "Genetic disease detrction and DNA amplification using cloned thermostable ligase", Proc Natl Acad Sci USA, Jan. 1991, vol. 88, pp. 189-193.
Champlot, "An Efficient Multistrategy PCR Applications", PLoS One, Sep. 2010, vol. 5, Issue 5, e13042, pp. 1-15.
Kramski, "Novel Sensitive Real-Time PCR for Quantification of Bacterial 16S rRNA Genes in Plasma of HIV-Infected Patients as a Marker for Microbial Translocation", J Clin Microbiol, Oct. 2011, vol. 49, No. 10, pp. 3691-93.
Shagin, "A Novel Method for SNP Detection Using a New Duplex-Specific Nuclease from Crab Hepatopancreas", Genome Res., Dec. 2002, 1935-42.
Nilsen et al., "The Enzyme and the cDNA Sequence of a Thermolabile and Double-Strand Specific DNase from Northern Shrimps (*Pandalus borealis*)", PLOS ONE, Apr. 2010, vol. 5, Issue 4, e10295, pp. 1-9.

(Continued)

*Primary Examiner* — Cynthia B Wilder
(74) *Attorney, Agent, or Firm* — Greenblum & Bernstein, P.L.C.

(57) ABSTRACT

It is an object of the present invention to provide a method for amplifying a nucleic acid, using RNA as a template, which can realize elimination of the risk of non-specific amplification caused by DNA mixed from reagents and/or working environment, an increase in the detection sensitivity of trace RNA, and a reduction in amplification bias. According to the present invention, there is provided a method for amplifying a nucleic acid, which comprises a step of incubating a mixture comprising template RNA, a primer, a degrading enzyme specific to DNA in RNA-DNA hybrid, an RNase H minus reverse transcriptase, and a substrate.

13 Claims, 12 Drawing Sheets

Specification includes a Sequence Listing.

(56) References Cited

OTHER PUBLICATIONS

Lee, "Experimental Murine Endometriosis Induces DNA Methylation and Altered Gene Expression in Eutopic Endometrium1", Biol Reprod. 80, Jan. 2009, pp. 79-85.
Voirin et al., "Versatile synthesis of oligodeoxyribonucleotide-oligospermine conjugates", Nat Protoc., 2007, vol. 2, No. 6, pp. 1360-1367.
Noir, "Oligonucleotide-oligospermine conjugates (zip nucleic acids): a convenient means of finely tuning hybridization temperatures", J Am Chem Soc., Sep. 10, 2008, vol. 130, No. 40, pp. 13500-13505.
Moreau, "Zip Nucleic Acids: new high affinity oligonucleotides as potent primers for PCR and reverse transcription", Nucleic Acids, published online Aug. 20, 2009, vol. 37, No. 19, e130, pp. 1-14.
Kelly, "DNA "melting" proteins. IV. Fluorescence measurements of binding parameters for bacteriophage T4 gene 32-protein to mono-, oligo-, and polyncleotides", J Biol Chem, Nov. 25, 1976, vol. 251, No. 22, pp. 7240-7250.
Chandler, "Reverse Transcriptase (RT) Inhibition of PCR at Low Concentrations of Template and Its Implications for Quantitative RT-PCR", Appl Environ Microbiol, Feb. 1998, vol. 64, No. 2, pp. 669-677.
Villalva, "Increased Yield of PCR Products by Addition of T4 Gene 32 Protein to the SMART-PCR cDNA Synthesis System", Biotehniques, Jul. 2001, vol. 31, No. 1, pp. 81-83, 86.
Boylan, "An Optimized Protocol for First Strand cDNA Synthesis from Laser Capture Microdissected Tissue", Lab Invest., Aug. 2001, vol. 81, No. 8, pp. 1167-1169.
Shimosato, "Extra-embryonic endoderm cells derived from ES cells induced by GATA factors acquire the character of XEN cells.", BMC Dev Biol., Jul. 3, 2007, 7:80, pp. 1-12.
Tuma, "Characterization of SYBR Gold nucleic acid gel stain: a dye optimized for use with 300-nm ultraviolet transilluminators.", Anal Biochem, Mar. 15, 1999, 268, pp. 278-288.
Kunitz, "Crystalline Desoxyribonuclease II. Digestion of Thymus Nucleic Acid (Desoxyribonucleic Acid) the Kinetics of the Reaction", J Gen Physiol., Mar. 1950, 33(4), pp. 363-377.
Campbell, "The effect of divalent cations on the mode of action of DNase I. The initial reaction products produced from covalently closed circlular DNA", J Biol Chem., 1980, vol. 255, No. 8, pp. 3726-3735.
Shamoo, "Crystal structure of a replication fork single-stranded DNA binding protein (T4 gp32)", Nature, Jul. 27, 1995, vol. 376, pp. 362-366.
Sasagawa et al., "Jisedai Genome Technology no. Tojo to sono Mirth 6.1 Saibo RNA-Seq-ho no Saizensen to Kongo no Tenkai", Experimental Medicine, Sep. 10, 2013, vol. 31, No. 15, pp. 2358-2364.
ISR issued in PCT/JP2015/077745, dated Dec. 15, 2015.
IPRP issued in PCT/JP2015/077745, dated Dec. 15, 2015.
Extended European Search Report from Application No. 15846028.7 dated Feb. 12, 2018.
Zaverucha-Do Valle et al., "Sustained effect of bone marrow mononuclear cell therapy in axonal regeneration in a model of optic nerve crush", 2014, pp. 54-68.
Gliozzi et al., "A link between interferon and augmented plasmin generation in exocrine gland damage in Sjogren's syndrome", 2013, pp. 122-133.
Holighaus et al., "PAC1hop, null and hit receptors mediate differential signaling though cyclic AMP and calcium leading to splice variant-specific gene induction in neural cells", 2011, pp. 1647-1655.
Office Action for EP App. No. 15 846 028.7 dated Dec. 18, 2018.
Office Action issued in EP 15 846 028.7 dated Aug. 29, 2019.

* cited by examiner

[Figure 1]
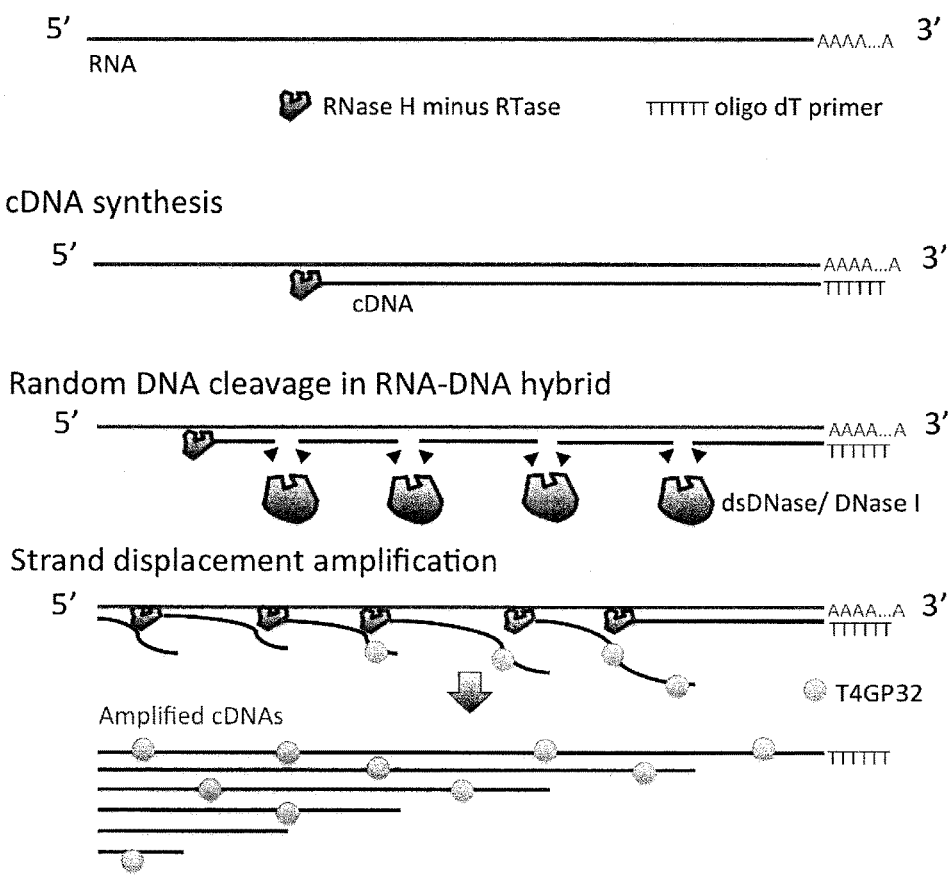

[Figure 2]
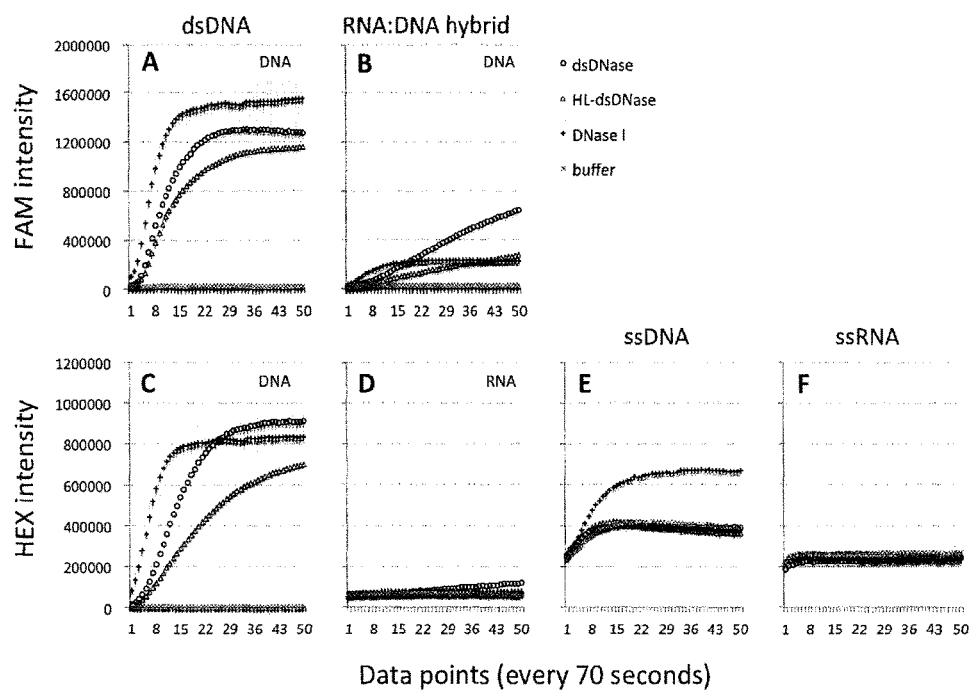

[Figure 3]
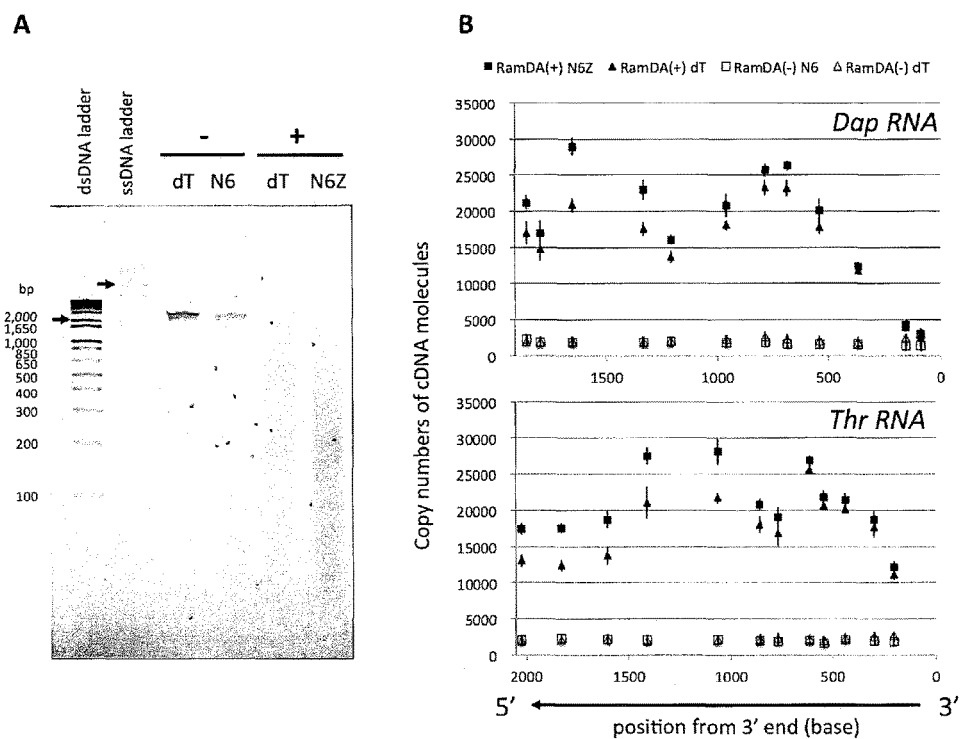

[Figure 4]
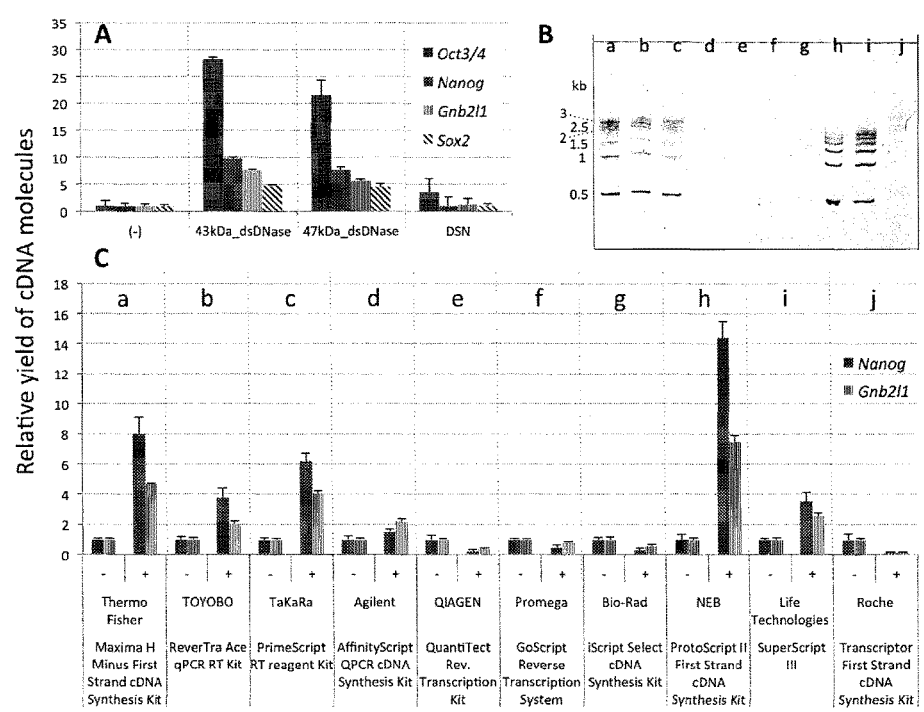

[Figure 5]
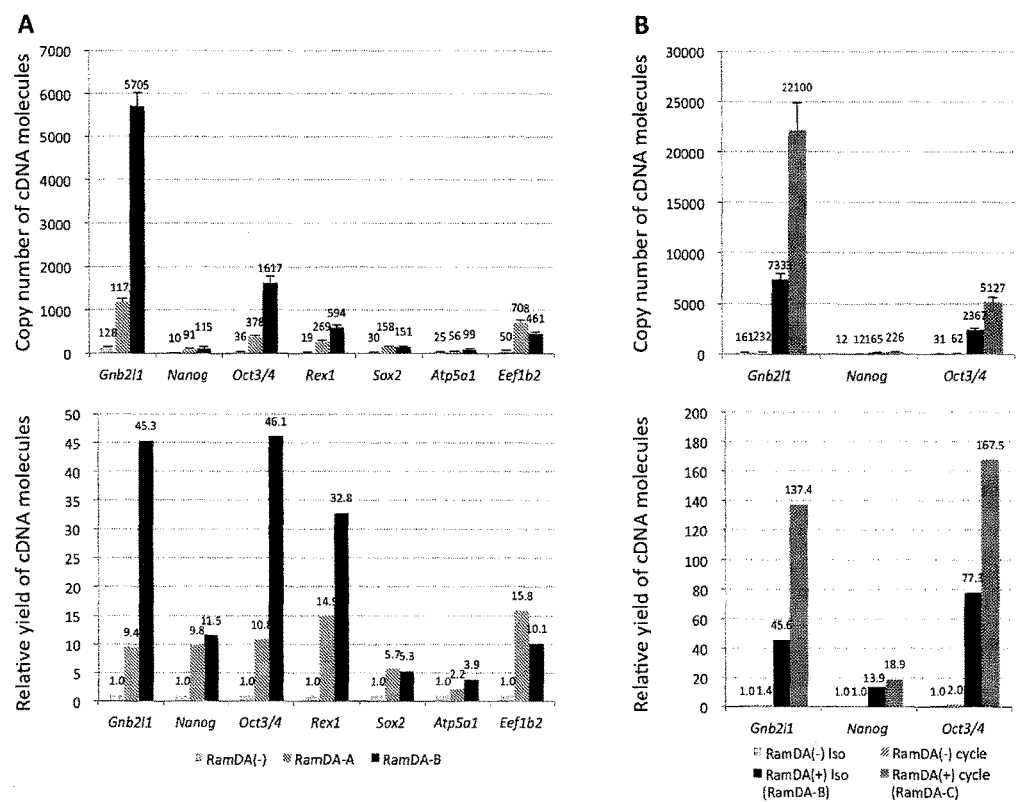

[Figure 6]
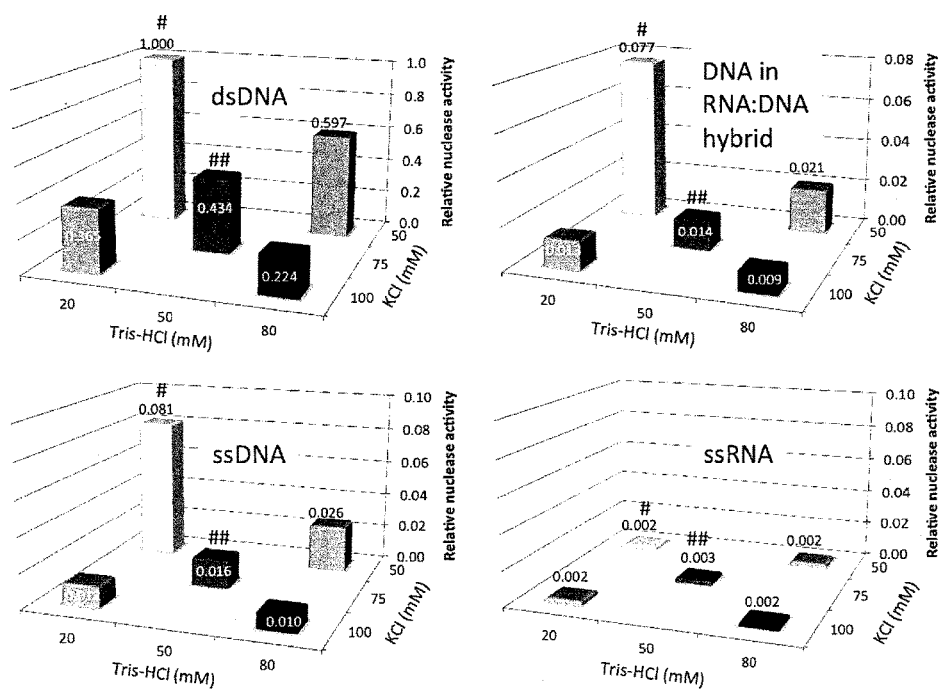

[Figure 7]
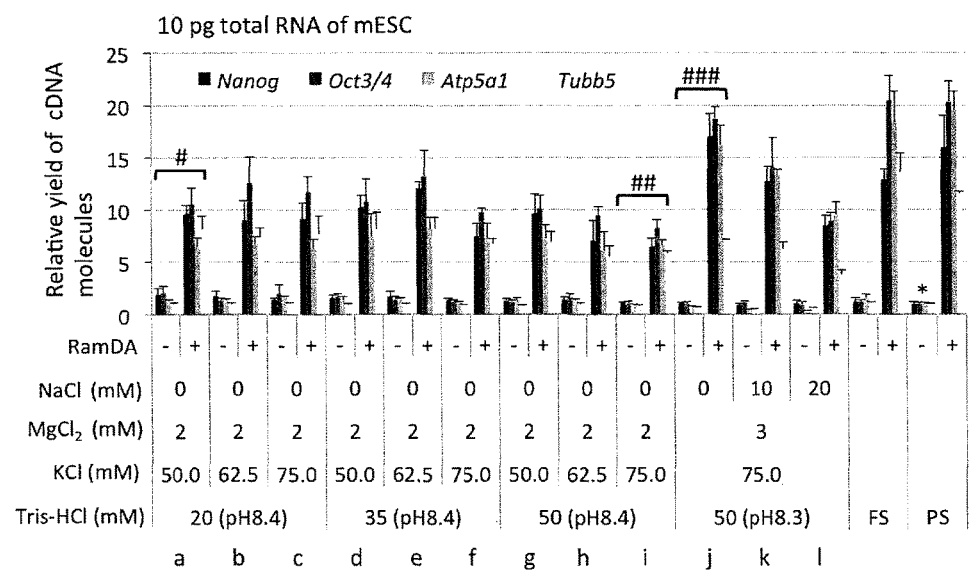

[Figure 8]
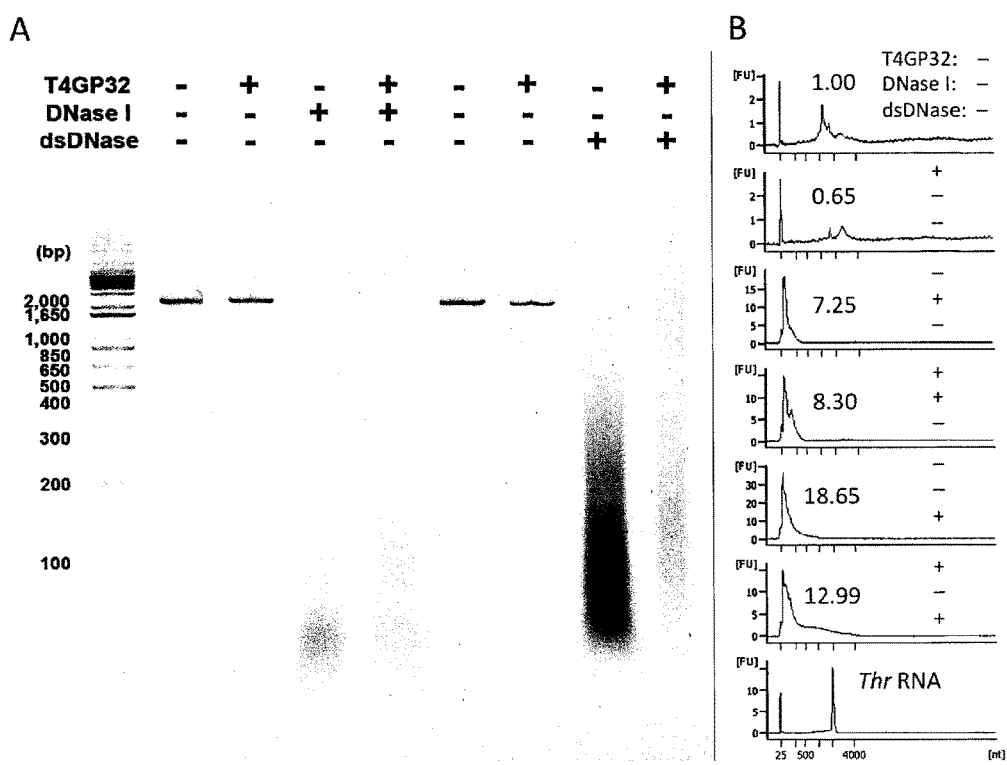

[Figure 9]
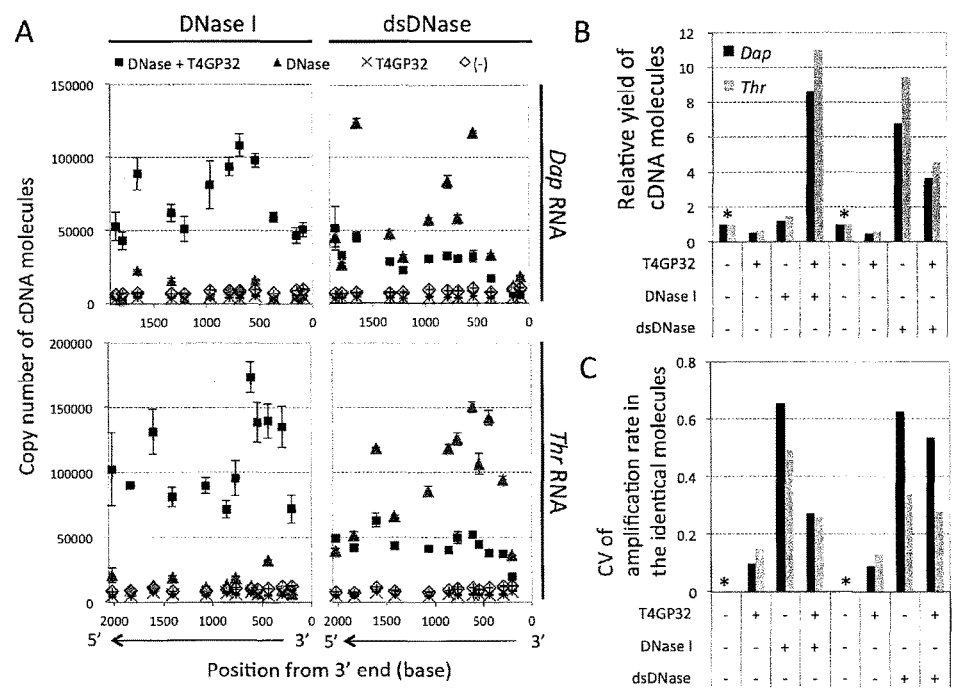

[Figure 10]
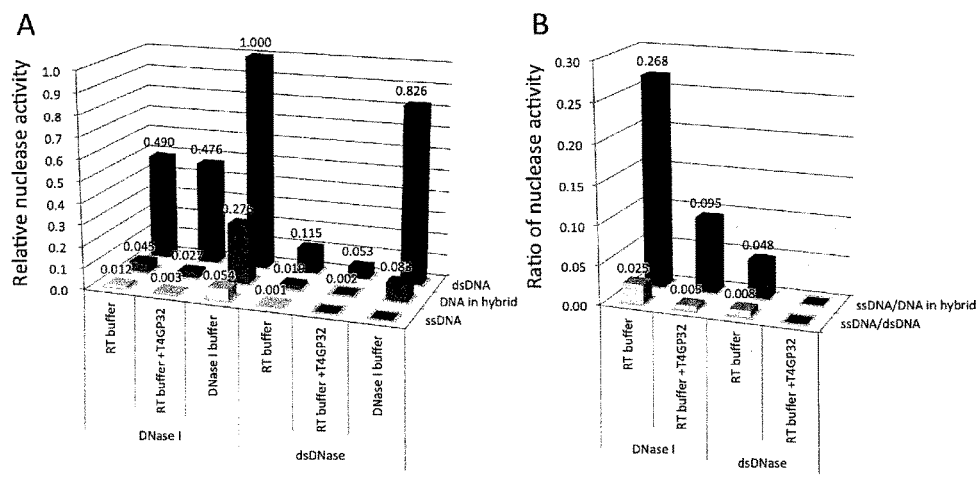

[Figure 11]
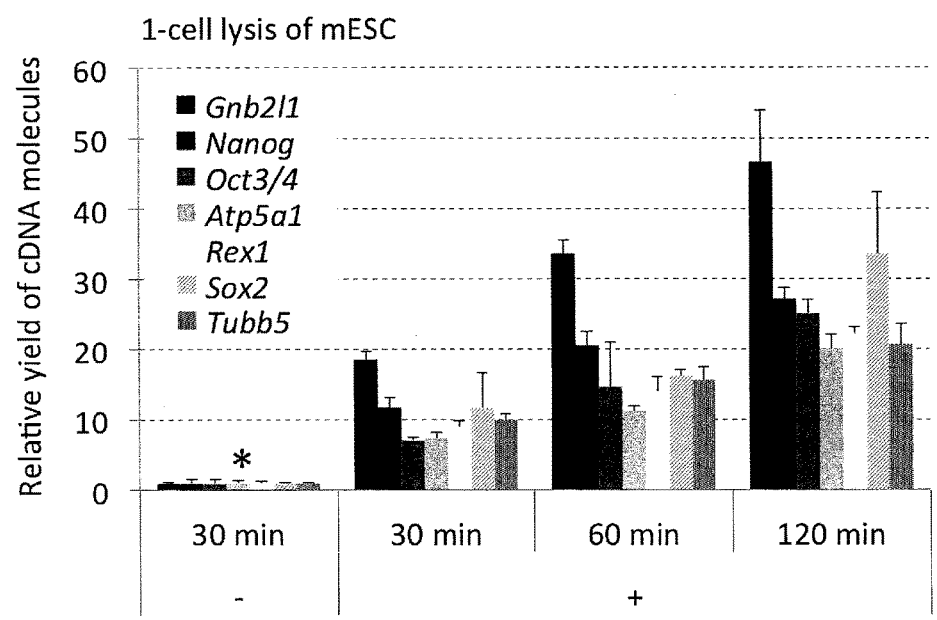

[Figure 12]
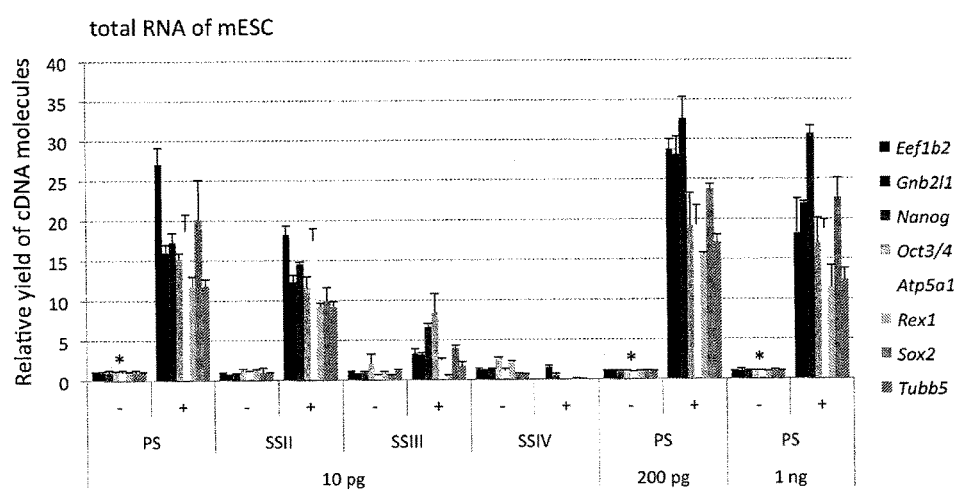

US 10,457,982 B2

METHOD FOR NUCLEIC ACID AMPLIFICATION

TECHNICAL FIELD

The present invention relates to a method for amplifying a nucleic acid, in which a degrading enzyme specific to DNA in RNA-DNA hybrid and a strand displacement activity are used. More specifically, the present invention relates to a method for amplifying a nucleic acid, using RNA as a template, and also using a degrading enzyme specific to DNA in RNA-DNA hybrid and an RNase H minus reverse transcriptase. Moreover, the present invention relates to a kit used for performing the above-described method for amplifying a nucleic acid.

BACKGROUND ART

A large number of methods for amplifying a nucleic acid have been reported so far. Examples of such a method for amplifying a nucleic acid include Polymerase Chain Reaction (PCR) (Non Patent Literature 1), Strand Displacement Amplification (SDA) (Non Patent Literature 2), Multiple Displacement Amplification (MDA) (Non Patent Literature 3), Rolling-Circle Amplification (RCA) (Non Patent Literature 4), Loop-Mediated Isothermal Amplification (LAMP) (Non Patent Literature 5), Smart Amplification Process (SmartAmp) (Non Patent Literature 6), Helicase-Dependent Amplification (HDA) (Non Patent Literature 7), and Ligase Chain Reaction (LCR) (Non Patent Literature 8). These methods are amplification methods of using DNA as a template, and in all of the methods other than PCR, HDA and LCR, the strand displacement activity of DNA polymerase is utilized. A main amplification system of utilizing a strand displacement reaction is SDA (Non Patent Literature 2). In SDA, a cleavage site (nick) is made on one strand of double-stranded DNA using a restriction enzyme or the like. Using this nick as a starting point, the DNA strand on the 3' side is peeled by the strand displacement activity of DNA polymerase, and novel complementary DNA is synthesized. SDA is a technique of amplifying complementary DNA by continuously generating this reaction. Moreover, MDA, which utilizes a random hexamer primer, is able to randomly take place a strand displacement reaction by randomly annealing primers to multiple sites on template DNA, and thus, this is a method having an extremely high amplification rate (Non Patent Literature 3). However, in order to amplify an RNA sequence according to these amplification methods using DNA as a template, it is necessary to perform a reverse transcription reaction of converting RNA to DNA. In addition, in the case of SDA, since a nick needs to be inserted into template DNA using restriction enzymes, it is necessary to add a restriction enzyme recognition sequence, deoxyinosine and the like to the template. Moreover, in the case of LAMP and SmartAmp, four or five sequence-specific primers are necessary for a single target. Thus, the synthesis of a special oligo primer, the designing of a sequence-specific primer, and the like become necessary. Furthermore, amplification methods using DNA as a template, such as PCR as a representative example, are problematic in terms of pseudo-positive results generated as a result of the carry-over of the previous PCR amplification products or reverse transcription products on samples, and non-specific products derived from DNA contaminated with reagents, DNA mixed from working environment, etc. (Non Patent Literatures 9 and 10). In particular, in the case of MDA, since primers are randomly annealed to DNA, it is likely that such contaminated DNA-derived non-specific products would be increased. As an amplification technique of using RNA as a template, a method of utilizing a special DNA hairpin primer having a restriction enzyme recognition sequence has been proposed. In this method, a cleavage point is generated on a DNA hairpin primer that has been allowed to bind to RNA as a template, and then, a strand displacement reaction is allowed to take place, so as to amplify complementary strand DNA. In this method, however, a pre-treatment needs to be performed to ligate a DNA hairpin primer to the 3'-end of template RNA, and thus, molecules that cannot be captured are likely to be generated depending on ligation conditions. Further, since amplification is started from the 3'-end of template RNA, it is considered difficult for this method to equally amplify the entire-length DNA.

PRIOR ART LITERATURES

Non Patent Literatures

Non Patent Literature 1: Specific Enzymatic Amplification of DNA In Vitro: The Polymerase Chain Reaction. Mullis Ket, al., Cold Spring Harb Symp Quant Biol. 1986; 51 Pt 1: 263-73.

Non Patent Literature 2: Isothermal in vitro amplification of DNA by a restriction enzyme/DNA polymerase system. Walker G T, et al., Proc Natl Acad Sci USA. 1992 Jan. 1; 89(1): 392-6.

Non Patent Literature 3: Comprehensive human genome amplification using multiple displacement amplification. Dean F B, et al., Proc Natl Acad Sci USA. 2002 Apr. 16; 99(8): 5261-6.

Non Patent Literature 4: Mutation detection and single-molecule counting using isothermal rolling-circle amplification. Lizardi P M, et al., Nat Genet. 1998 July; 19(3): 225-32.

Non Patent Literature 5: Loop-mediated isothermal amplification of DNA. Notomi T, et al., Nucleic Acids Res. 2000 Jun. 15; 28(12): E63.

Non Patent Literature 6: Rapid SNP diagnostics using asymmetric isothermal amplification and a new mismatch-suppression technology. Mitani Y, et al., Nat Methods. 2007 March; 4(3): 257-62. Epub 2007 Feb. 18.

Non Patent Literature 7: Helicase-dependent isothermal DNA amplification. Myriam Vincent, et al., EMBO Rep. 2004 August; 5(8): 795-800.

Non Patent Literature 8: Genetic disease detection and DNA amplification using cloned thermostable ligase. Barany F. Proc Natl Acad Sci USA. 1991 Jan. 1; 88(1): 189-93.

Non Patent Literature 9: An Efficient Multistrategy DNA Decontamination Procedure of PCR Reagents for Hypersensitive PCR Applications. Champlot S, et al., PLoS One. 2010 Sep. 28; 5(9).

Non Patent Literature 10: Novel Sensitive Real-Time PCR for Quantification of Bacterial 16S rRNA Genes in Plasma of HIV-Infected Patients as a Marker for Microbial Translocation. Kramski M, et al., J Clin Microbiol. 2011 October; 49(10)

Non Patent Literature 11: A Novel Method for SNP Detection Using a New Duplex-Specific Nuclease From Crab Hepatopancreas. Shagin D A, et al., Genome Res. 2002 December; 12(12): 1935-42

Non Patent Literature 12: The Enzyme and the cDNA Sequence of a Thermolabile and Double-Strand Specific DNase from Northern Shrimps (*Pandalus borealis*). Nilsen I W, et al., PLoS One. 2010 Apr. 22; 5(4): e10295.

Non Patent Literature 13: Experimental Murine Endometriosis Induces DNA Methylation and Altered Gene Expression in Eutopic Endometriuml. Lee B, et al., Biol Reprod. 2009 January; 80(1): 79-85.

Non Patent Literature 14: Versatile synthesis of oligodeoxyribonucleotide-oligospermine conjugates. Voirin E, Behr J P, et al., Nat Protoc. 2007; 2(6): 1360-7.

Non Patent Literature 15: Oligonucleotide-oligospermine conjugates (zip nucleic acids): a convenient means of finely tuning hybridization temperatures. Noir R, et al., J Am Chem Soc. 2008 Oct. 8; 130(40): 13500-5.

Non Patent Literature 16: Zip Nucleic Acids: new high affinity oligonucleotides as potent primers for PCR and reverse transcription. Moreau V, et al., Nucleic Acids Res. 2009 October; 37(19)

Non Patent Literature 17: DNA "melting" proteins. IV. Fluorescence measurements of binding parameters for bacteriophage T4 gene 32-protein to mono-, oligo-, and polynucleotides. Kelly R C, et al., J Biol Chem. 1976 Nov. 25; 251(22): 7240-50.

Non Patent Literature 18: Reverse Transcriptase (RT) Inhibition of PCR at Low Concentrations of Template and Its Implications for Quantitative RT-PCR. Chandler D P, et al., Appl Environ Microbiol. 1998 February; 64(2): 669-77.

Non Patent Literature 19: Increased Yield of PCR Products by Addition of T4 Gene 32 Protein to the SMART-PCR cDNA Synthesis System. Villalva C, et al., Biotechniques. 2001 July; 31(1): 81-3, 86.

Non Patent Literature 20: An Optimized Protocol for First Strand cDNA Synthesis from Laser Capture Microdissected Tissue. Boylan S, et al., Lab Invest. 2001 August; 81(8): 1167-9.

Non Patent Literature 21: Extra-embryonic endoderm cells derived from ES cells induced by GATA factors acquire the character of XEN cells. Shimosato D, et al., BMC Dev Biol. 2007 Jul. 3; 7: 80.

Non Patent Literature 22: Characterization of SYBR Gold nucleic acid gel stain: a dye optimized for use with 300-nm ultraviolet transilluminators. Tuma R S, et al., Anal Biochem. 1999 Mar. 15; 268(2): 278-88.

Non Patent Literature 23: CRYSTALLINE DESOXYRIBONUCLEASE II. DIGESTION OF THYMUS NUCLEIC ACID (DESOXYRIBONUCLEIC ACID) THE KINETICS OF THE REACTION. Kunitz M, J Gen Physiol. 1950 March; 33(4): 363-77.

Non Patent Literature 24: The effect of divalent cations on the mode of action of DNase I. The initial reaction products produced from covalently closed circular DNA. Campbell V W, et al., J Biol Chem. 1980 Apr. 25; 255(8): 3726-35.

Non Patent Literature 25: Crystal structure of a replication fork single-stranded DNA binding protein (T4 gp32) complexed to DNA. Shamoo Y, et al., Nature. 1995 Jul. 27; 376(6538): 362-6.

SUMMARY OF INVENTION

Object to be Solved by the Invention

To perform a gene expression analysis, it is necessary to convert RNA to complementary DNA (cDNA). There has been an amplification technique of using DNA as a template, but there have been no amplification techniques of directly using, as a template, untreated RNA that has not been subjected to a pre-treatment such as addition of a special sequence. It is an object of the present invention to provide, not the existing amplification method of using DNA as a template, but a method for amplifying a nucleic acid, using RNA as a template. That is, it is an object of the present invention to provide a method for amplifying a nucleic acid, using RNA as a template, which can realize not only simplification of operations, but also elimination of the risk of non-specific amplification caused by DNA contaminated with reagents and/or working environment, an increase in the detection sensitivity of trace RNA, and a reduction in amplification bias.

Means for Solving the Object

As a result of intensive studies directed towards achieving the aforementioned object, the present inventors have discovered a reverse transcription method with random displacement amplification (hereinafter also referred to as a "RT-RamDA method," or simply a "RamDA method"), in which cDNA is amplified using RNA as a template. It have been revealed that, according to the RT-RamDA method, the yield of cDNA can be increased to 10 to 100 times as compared to a commercially available kit, and that it becomes possible to capture low expressed genes or to increase the number of detected genes in a gene expression analysis from a trace amount of RNA. Moreover, the cDNA amplified by the RamDA method can be applied to various gene analyses such as an RNA sequence method, and thus, it is expected that the RamDA method will be used as a basic technique of molecular biology in a wide range of fields. Furthermore, differing from the existing amplification technology of using DNA as a template, the use of RNA as a template can realize not only simplification of operations, but also elimination of the risk of non-specific amplification caused by DNA contaminated with reagents and/or working environment, and a reduction in amplification bias. The present invention has been completed based on these findings.

Specifically, according to the present invention, the following inventions are provided.

(1) A method for amplifying a nucleic acid, comprising a step of incubating a mixture containing template RNA, a primer, a degrading enzyme specific to DNA in RNA-DNA hybrid, an RNase H minus reverse transcriptase, and a substrate, wherein the degrading enzyme specific to DNA in RNA-DNA hybrid has an activity of cleaving a DNA strand in the RNA-DNA hybrid.

(2) The method for amplifying a nucleic acid according to (1), which comprises a step of synthesizing a complementary strand DNA (cDNA) of the template RNA by the RNA-dependent DNA polymerase activity of the RNase H minus reverse transcriptase, then randomly cleaving the cDNA strand in the hybrid strand of RNA and cDNA by the degrading enzyme specific to DNA in RNA-DNA hybrid, then peeling the cDNA strand on the 3' side from the RNA by the strand displacement activity of the RNase H minus reverse transcriptase, while using the cleavage site as a starting point, and then synthesizing a novel cDNA strand in a portion peeled by the RNase H minus reverse transcriptase.

(3) The method for amplifying a nucleic acid according to (1) or (2), wherein the mixture comprises a double strand-specific DNA degrading enzyme as a degrading enzyme specific to DNA in RNA-DNA hybrid, and the double strand-specific DNA degrading enzyme has an activity of cleaving the DNA strand in the RNA-DNA hybrid, and substantially does not have an activity of cleaving the RNA strand in the RNA-DNA hybrid, single-stranded DNA and single-stranded RNA.

(4) The method for amplifying a nucleic acid according to (1) or (2), wherein the mixture comprises a non-specific DNA degrading enzyme as a degrading enzyme specific to DNA in RNA-DNA hybrid, and the non-specific DNA degrading enzyme has an activity of cleaving the DNA strand of the RNA-DNA hybrid strand, and substantially does not have an activity of cleaving the RNA strand in the RNA-DNA hybrid, and single-stranded RNA.

(5) The method for amplifying a nucleic acid according to any one of (1) to (4), wherein the degrading enzyme specific to DNA in RNA-DNA hybrid has a DNA-degrading activity even at a temperature of lower than 60° C.

(6) The method for amplifying a nucleic acid according to (3), wherein the double strand-specific DNA degrading enzyme is a double strand-specific DNA degrading enzyme derived from Crustacea, or a variant thereof.

(7) The method for amplifying a nucleic acid according to (6), wherein the double strand-specific DNA degrading enzyme is a double strand-specific DNA degrading enzyme derived from a shrimp, or a variant thereof.

(8) The method for amplifying a nucleic acid according to (4), wherein the non-specific DNA degrading enzyme is a non-specific DNA degrading enzyme derived from a mammal, or a variant thereof.

(9) The method for amplifying a nucleic acid according to (8), wherein the non-specific DNA degrading enzyme is a non-specific DNA degrading enzyme derived from a bovine, or a variant thereof.

(10) The method for amplifying a nucleic acid according to any one of (1) to (9), wherein the primer is one or more of a random primer, an oligo dT primer and a sequence-specific primer.

(11) The method for amplifying a nucleic acid according to any one of (1) to (10), wherein the primer is a primer, the Tm value of which is increased by modification with a cation unit.

(12) The method for amplifying a nucleic acid according to any one of (1) to (11), wherein the primer is a Zip Nucleic Acid (ZNA) primer.

(13) The method for amplifying a nucleic acid according to any one of (1) to (12), wherein the mixture further comprises a single-stranded DNA-binding protein.

(14) The method for amplifying a nucleic acid according to any one of (1) to (13), wherein the template RNA is trace RNA corresponding to a volume ranging from a single cell to several hundreds of cells.

(15) The method for amplifying a nucleic acid according to any one of (1) to (14), which is performed to amplify cDNA that is to be subjected to the production of a DNA sequence library.

(16) A kit used for performing the method for amplifying a nucleic acid according to any one of (1) to (15), wherein the kit comprises, at least, a degrading enzyme specific to DNA in RNA-DNA hybrid and an RNase H minus reverse transcriptase.

(17) The kit according to (16), which further comprises a single-stranded DNA-binding protein.

Advantageous Effects of Invention

Since a nucleic acid can be amplified using RNA as a template according to the method for amplifying a nucleic acid of the present invention, the present method can realize not only simplification of operations, but also elimination of the risk of non-specific amplification caused by DNA contaminated with reagents and/or working environment, and a reduction in amplification bias. Moreover, according to the method for amplifying a nucleic acid of the present invention, the yield that is 10 times or more the yield as compared to the existing reverse transcription cDNA synthesis kit can be obtained, and it is also possible to perform amplification at a magnification of 100 times or more, depending on conditions.

BRIEF DESCRIPTION OF DRAWINGS

FIG. 1 is a schematic view of an RT-RamDA (RamDA) method.

FIG. 2 shows that a double strand-specific DNA degrading enzyme (dsDNase) and a non-specific DNA degrading enzyme (DNase I) cleave not only double-stranded DNA, but also DNA in an RNA-DNA hybrid. According to FRET analysis using a fluorescent oligonucleotide, dsDNase and DNase I were examined in terms of the properties of nuclease under reserve transcription buffer conditions. The nuclease activity was measured over time under four conditions, namely, dsDNase, DNase I, HL-dsDNase having thermal instability, and a buffer control (buffer) that did not contain DNase. FIGS. 2A and 2C show the activity in DNA of double-stranded DNA, FIG. 2B shows the activity in DNA of an RNA-DNA hybrid, and FIG. 2D shows the activity in RNA of the hybrid. FIGS. 2E and 2F show the results of the activity in single-stranded DNA and in single-stranded RNA, respectively. The measurement was carried out by performing detection 50 times, at 37° C. every 70 seconds. The error bar indicates a standard deviation (n=3).

FIG. 3 shows that fragmentation and amplification of cDNA take place by the activity of dsDNase. In FIG. 3A, using 5 ng of artificially synthesized RNA, Thr RNA (2,052 b), as a template, the cDNA pattern of a standard reverse transcription method (RamDA (−)) and the cDNA pattern of RamDA (+) involving addition of dsDNase, a ZNA-random hexamer primer and a T4 gene 32 protein to the standard reverse transcription method were examined by agarose gel electrophoresis. The ssDNA ladder is a thermally denatured dsDNA ladder. The arrows each indicate 2 kb. In the figure, the symbol "−" indicates RamDA (−), and the symbol "+" indicates RamDA (+). In FIG. 3B, the amount of cDNA in 100 fg of artificially synthesized RNAs, Dap RNA (96,725 copies) and Thr RNA (89,991 copies), which were added to 10 pg of total RNA derived from mouse ES cells that was the amount of total RNA corresponding to a single cell, was detected by qPCR. For the qPCR, a reverse transcription product was used in an amount of 1/50. The horizontal axis indicates the distance from the 3' end. Regarding qPCR primers for detection, the primers for Dap and Thr were each designed in 12 regions from 5' to 3'. dT: an oligo dT primer, N6: a random hexamer primer, and N6Z: a ZNA-random hexamer primer. The error bar indicates a standard deviation (n=3).

FIG. 4 shows that an RT-RamDA method acts with thermally unstable dsDNase and RNase H minus reverse transcriptase. In FIG. 4A, the detected amount of cDNA in the case of using, as a template, 10 pg of total RNA derived from mouse ES cells is shown as a relative quantitative value using qPCR. The value indicates a relative value to the amount of cDNA (copy number) detected in each gene under RamDA (−) conditions. The error bar indicates a standard deviation (n=4). FIG. 4B shows the agarose gel electrophoresis patterns of cDNAs synthesized by using, as templates, 20 ng of MillenniumRNA Markers (0.5, 1, 1.5, 2, 2.5, 3, 4, 5, 6, and 9 kb) and by employing various types of reverse transcriptase kits. The alphabets a to j correspond to a to j in the graph shown in FIG. 4C. A band forming an RNA-DNA hybrid strand is stained brightly than single-stranded cDNA (Non Patent Literature 21). The elongation reaction was carried out at 42° C. for 2.5 minutes. In FIG. 4C, the detected amount of cDNA in the case of using, as a template, 10 pg of total RNA derived from mouse ES cells is shown as a relative quantitative value using qPCR. In the figure, the symbol "−" indicates RamDA (−), and the symbol "+" indicates RamDA (+). The value of RamDA (−) for each enzyme was defined as 1. In RamDA (+) for each of a to c, h and i, amplification was observed at a magnification of 2 times or more. The error bar indicates a standard deviation (n=4).

FIG. 5 shows that RamDA-B and RamDA-C exhibit extremely high amplification rates in specific genes. FIG. 5A shows the amount of cDNA detected by qPCR using, as a template, 10 pg of total RNA derived from mouse ES cells (upper case) and the relative value obtained when RamDA (−) is set at 1 (lower case). The error bar indicates a standard deviation (n=4). FIG. 5B shows the effects of thermal cycling. The figure shows the amount of cDNA detected by qPCR using, as a template, 10 pg of total RNA derived from mouse ES cells (upper case) and the relative value obtained when RamDA (−) under isothermal conditions is set at 1 (lower case). The error bar indicates a standard deviation (n=3). In the figure, "RamDA (−) iso" and "RamDA (+) iso" indicate isothermal conditions (the same conditions as those of RamDA-A), and "RamDA (−) cycle" and "RamDA (+) cycle" indicate thermal cycling conditions.

FIG. 6 shows a decrease in the nuclease activity of DNase I in a Tris-HCl and KCl concentration-dependent manner. According to FRET analysis using a fluorescent oligonucleotide, the nuclease activity of DNase I was measured. With regard to the fluorescent oligonucleotide, the fluorescent amount was measured using one color of FAM label probe at 37° C. every 1 minute. The nuclease activity was calculated based on the fluorescence increase rate in the initial stage of reaction (5-10 minutes). The activity was indicated as a relative value, when the activity to double-stranded DNA in a DNase I buffer (50 mM Tris-HCl, 75 mM KCl, and 2 mM MgCl2) was set at 1. The value was calculated based on the mean value of n=3. The symbol # indicates the concentration of a DNase I buffer. The symbol ## indicates the concentration of Tris-HCl and KCl that is the same as that of a common reverse transcription buffer. dsDNA: double-stranded DNA; DNA in RNA:DNA hybrid: DNA in a hybrid strand of RNA and DNA; ssDNA: single-stranded DNA; and ssRNA: single-stranded RNA.

FIG. 7 shows that an RT-RamDA method of using DNase I (RamDA-D) is not limited to a specific reaction buffer composition. The yield of cDNA in an RT-RamDA method of using DNase I and also using, as a template, 10 pg of total RNA derived from mouse ES cells, was quantified by qPCR. The symbol # indicates the same reaction buffer composition as that of a DNase I buffer. The symbol ## indicates the concentration of Tris-HCl and KCl that is the same as that of a common reverse transcription reaction buffer. The symbol ### indicates the same composition as that of a common reverse transcription reaction buffer, such as First-Strand buffer. FS: First-Strand Buffer. PS: PrimeScript Buffer (for Real Time). Setting RamDA (−) of using PrimeScript Buffer (for Real Time) as a control (*), the yield of cDNA is indicated as a relative value, when the amount of cDNA detected in each gene in the control is set at 1. The error bar indicates a standard deviation (n=4). Amplification takes place even in the same composition (#) as that of a DNase I buffer having high activity of DNase I to single-stranded DNA. Rather, the amplification rate is higher than under conditions in which the activity to single-stranded DNA is low (##).

FIG. 8 shows that a T4 gene 32 protein suppresses fragmentation of cDNA by DNase I. In FIG. 8A, using 5 ng of Thr RNA (2,052 b) as a template, cDNA distribution patterns were compared under conditions of a non-added standard reverse transcription sample, single addition of a T4 gene 32 protein, single addition of DNase I or dsDNase, and simultaneous addition of a T4 gene 32 protein with DNase I or dsDNase. The reverse transcription reaction was carried out in a reaction volume of 6 µl that is two times of ordinary amount, using only an oligo dT primer. The distribution pattern of cDNA was examined by 2% agarose gel electrophoresis. FIG. 8B shows the results obtained by analyzing the cDNA of FIG. 8A that was in an amount of 1/20 of FIG. 8A, using BioAnalyzer RNA 6000 Pico Kit (Agilent Biotechnology). The numerical values in the figure each show a relative value of the cDNA concentration. T4GP32: T4 gene 32 protein.

FIG. 9 shows that a T4 gene 32 protein contributes to amplification of cDNA and the stability thereof. The figure shows the amount of cDNA in 100 fg of artificially synthesized RNAs, Dap RNA (96,725 copies) and Thr RNA (89,991 copies), which were added to 10 pg of Universal Human Reference RNA (UHRR). The reverse transcription reaction was carried out using only an oligo dT primer, and the yield of cDNA was quantified using qPCR. DNase I and dsDNase were used in amounts of 0.2 U and 0.4 U, respectively, and the T4 gene 32 protein was used in an amount of 100 ng for a single reaction. The qPCR was carried out using the reverse transcription product in an amount of 1/50. Regarding qPCR primers for detection, the primers for Dap and Thr were each designed in 12 regions from 5' to 3'. FIG. 9A shows the amount of cDNA (copy number) detected in each region. The horizontal axis indicates the distance from the 3' end. (−): control (a non-added standard reverse transcription sample), and the error bar indicates a standard deviation (n=3). FIG. 9B shows a relative value, when the detected amount in each region of the non-added control sample (*) is set at 1. FIG. 9C shows a fluctuation in the relative values (amplification rates) of the detection amounts on the same RNA. T4GP32: T4 gene 32 protein.

FIG. 10 shows the effect of a T4 gene 32 protein on nuclease activity in a reverse transcription reaction buffer, which was examined by FRET analysis using fluorescent oligonucleotides. As such fluorescent oligonucleotides, two colors, namely, FAM or HEX label probe, were used, and the fluorescence intensity was measured at 37° C. every 1.5 minutes. The nuclease activity was calculated based on the fluorescence increase rate in the initial stage of reaction (1.5-9 minutes) (a mean value of n=3). As a reserve transcription buffer, PrimeScript buffer was used. FIG. 10A indicates a relative value of nuclease activity, when the activity of DNase I on double-stranded DNA in a DNase I buffer is set at 1. FIG. 10B shows the ratio of single-stranded DNA-degrading activity to DNA-degrading activity in an RNA-DNA hybrid, or to double-stranded DNA-degrading activity, in individual reaction conditions. dsDNA: double-stranded DNA; DNA in hybrid: DNA in the RNA-DNA hybrid; ssDNA: single-stranded DNA; and ssRNA: single-stranded RNA.

FIG. 11 shows an increase in the yield of cDNA in a reaction time-dependent manner, in RamDA-D of using a 1-cell lysate of mouse ES cells. Among the reaction temperature conditions for RamDA-D, 37° C. was applied, the reaction time at 37° C. was prolonged to 30 minutes, 60 minutes, and 120 minutes, and the influence of the reaction time on the amplification rate was then examined. Using the reaction time of 30 minutes in RamDA-D (−) as a control (*), a relative value is shown, when the amount of cDNA detected in each gene by qPCR is set at 1. The error bar indicates a standard deviation (n=4).

FIG. 12 shows that, in RamDA-D, amplification can be carried out, even if the type of reverse transcriptase is not limited and template RNA is used in an amount corresponding to 100 cells. Setting the RamDA (−) condition of PrimeScript as a control (*), a relative value is shown, when the amount of cDNA detected in each gene by qPCR is set at 1. As template RNA, total RNA derived from mouse ES cells (10 pg, 200 pg, or 1 ng) was used. PS: PrimeScript RT Enzyme; SSII: SuperScript II RT Enzyme; SSIII: SuperScript III RT Enzyme; and SSIV: SuperScript IV RT Enzyme. The error bar indicates a standard deviation (n=4).

EMBODIMENTS FOR CARRYING OUT THE INVENTION

Hereinafter, the present invention will be more specifically described.

The method for amplifying a nucleic acid according to the present invention is carried out by incubating a mixture comprising template RNA, a primer, a degrading enzyme specific to DNA in RNA-DNA hybrid an RNase H minus reverse transcriptase, and a substrate, and this method is also referred to as Reverse Transcription with Random Displacement Amplification (RT-RamDA) Method. The method for amplifying a nucleic acid of the present invention is a reverse transcription method with random displacement amplification, in which a strand displacement reaction is utilized and RNA is directly used as a template, and this method can be carried out in vitro. The method of the present invention is a technique of amplifying cDNA in a reverse transcription reaction, whereby the cDNA strand in the RNA-cDNA hybrid is cleaved by utilizing the nuclease activity of a degrading enzyme specific to DNA in RNA-DNA hybrid as endonuclease, such as a double strand-specific DNA degrading enzyme (double-strand specific DNase: dsDNase) or a non-specific DNA degrading enzyme (DNase I), so that a strand displacement reaction is allowed to randomly take place.

In the present description, the term "amplification" is used to mean to increase the number of copies (replications) of the sequence of a nucleic acid. In addition, examples of the form of amplification include linear amplification, real-time amplification, quantitative amplification, semi-quantitative amplification, and competitive amplification, but are not particularly limited thereto.

The mixture used in the present invention is a mixture comprising template RNA, a primer, a degrading enzyme specific to DNA in RNA-DNA hybrid, an RNase H minus reverse transcriptase, and a substrate. The present mixture is preferably an aqueous buffer, and more preferably an aqueous buffer comprising salts.

An outline of one aspect of the RT-RamDA method of the present invention will be described below (FIG. 1).
1. The complementary DNA (cDNA) of template RNA is synthesized by the RNA-dependent DNA polymerase activity of an RNase H minus reverse transcriptase.
2. A cleavage point (nick) is randomly made in the cDNA strand in the RNA-cDNA hybrid by the nuclease activity of a degrading enzyme specific to DNA in RNA-DNA hybrid, such as a double strand-specific DNA degrading enzyme (dsDNase) or a non-specific DNA degrading enzyme (DNase I).
3. The nick site becomes a starting point, and the cDNA strand on the 3' side is peeled by the strand displacement activity of the RNase H minus reverse transcriptase. cDNA is newly synthesized in the peeled portion by reverse transcriptase. The peeled cDNA is protected from the nuclease activity by a T4 gene 32 protein (T4GP32) as a single-stranded DNA-binding protein. When this phenomenon takes place continuously, the yield of cDNA can be increased to 10-fold or more.

Since the RNA-DNA hybrid strand is targeted by the degrading enzyme specific to DNA in RNA-DNA hybrid in the method for amplifying a nucleic acid of the present invention, or since the template is RNA in the strand displacement amplification reaction, the available reverse transcriptase is limited to those having no RNase H activity. The RNase H activity is ribonuclease activity of randomly cleaving only the RNA strand in an RNA-DNA hybrid. RNase H is non-specific endonuclease, which catalyzes RNA cleavage by hydrolysis.

Moreover, the RNase H minus reverse transcriptase used in the present invention has a strand displacement activity. The cDNA strand on the 3' side is peeled from RNA by the strand displacement activity of the RNase H minus reverse transcriptase, and a new cDNA strand is synthesized in the peeled portion.

The reverse transcription is a process in which reverse transcriptase (RNA-dependent DNA polymerase) catalyzes the formation of complementary DNA (cDNA) from template RNA. As such reverse transcriptase, a large number of enzymes have been identified, and examples of the reverse transcriptase include HIV reverse transcriptase, AMV reverse transcriptase, M-MLV reverse transcriptase, C therm. polymerase, and Tth polymerase. In the present invention, RNase H minus reverse transcriptase is used.

In the present invention, a degrading enzyme specific to DNA in RNA-DNA hybrid is used. The term "degrading enzyme specific to DNA in RNA-DNA hybrid" is used in the present description to mean an enzyme having an activity of cleaving a DNA strand in a hybrid strand of RNA and DNA (RNA-DNA hybrid). As such a degrading enzyme specific to DNA in RNA-DNA hybrid, a double strand-specific DNA degrading enzyme or a non-specific DNA degrading enzyme can be used. As a double strand-specific DNA degrading enzyme, a crab-derived double strand-specific DNA degrading enzyme (double strand-specific nuclease; DSN) has been known. This enzyme randomly cleaves not only double stranded DNA, but also only the DNA strand in an RNA-DNA hybrid. In the present invention, there has been proposed a method of utilizing the aforementioned activity to cleave the cDNA in an RNA-cDNA hybrid formed during reverse transcription, so as to cause strand displacement amplification while using RNA as a template. However, since the temperature for activation of crab-derived DSN is an extremely high temperature that is 60° C. or higher, it is unsuitable for a general reverse transcription reaction (Non Patent Literature 11). Hence, by using shrimp-derived heat-labile dsDNase that is active even at a low temperature, both a reverse transcription reaction and cleavage with DNase could be achieved (Non Patent Literature 12). On the other hand, when a non-specific DNA degrading enzyme such as DNase I is used, single-stranded DNA, namely, amplified DNA that is peeded by a strand displacement reaction or a reverse transcription primer is likely to be decomposed. However, even if the enzyme has an activity of degrading single-stranded DNA, it is a case where it would not cause a problem, depending on reaction conditions such as the composition of a buffer used. Whether or not the enzymes used or reaction conditions are suitable can be confirmed by performing a nucleic acid amplification reaction according to the disclosure of the present description. Moreover, by addition of a single-stranded DNA-binding protein, the degradation activity of single-stranded DNA is suppressed, and the synthesis and amplification of cDNA can be promoted by a strand displacement reaction using reverse transcriptase. As such a single-stranded DNA-binding protein, any given protein, which binds to single-stranded DNA to increase the efficiency of nucleic acid amplification according to the method of the present invention, can be used, and for example, any given origin-derived T4 gene 32 protein, RecA, SSB (Single-Stranded DNA Binding Protein), or a variant thereof can be used. Thereby, the amplification rate can be increased, rather than by a method of using dsDNase. The use of dsDNase or DNase I is advantageous in that DNA contaminated with the reaction solution, for example, genomic DNA in a cell lysate sample can also be removed. Also in the past, there have been reported methods of removing contaminated DNA using DNase I or dsDNase in RT-qPCR. However, in a majority of such methods, inactivation of nuclease has been essential, and thus, such methods could not be carried out by only one step consisting of a reverse transcription reaction, like the RT-RamDA method (Non Patent Literature 13).

There have been many reports regarding DNA amplification methods using a strand displacement reaction, as with the RT-RamDA method (for example, Non Patent Literatures 2 to 6). However, a majority of these amplification methods including SDA as a typical example need to use restriction enzymes to insert a nick into template DNA, or need to use a plurality of sequence-specific primers in combination. Accordingly, it is essential to add a restriction enzyme recognition sequence or deoxyinosine to template DNA, or to design and/or synthesize a sequence-specific primer. Moreover, target genes are also limited. Furthermore, since almost all of existing methods use DNA as a template, it is necessary to perform a reverse transcription reaction of converting RNA to DNA in order to amplify an RNA sequence. Further, pseudo-positive results generated as a result of the carry-over of the previous PCR amplification products or reverse transcription products on samples, and non-specific products derived from DNA contaminated with reagents, DNA mixed from working environment, etc., have been problematic (Non Patent Literatures 9 and 10). In particular, in MDA, since a primer is randomly annealed to DNA, it is highly likely that the contaminated DNA-derived non-specific products would be increased. On the other hand, the RT-RamDA method of the present invention uses a non-sequence-dependent strand displacement reaction, and thus, it becomes unnecessary to design and/or synthesize a sequence-specific primer or a special primer, and also, it can target whole genes. Furthermore, by directly using RNA as a template, the process from reverse transcription to amplification can be completed by only one step, and since DNA hardly becomes a template, amplification of non-specific products derived from the contaminated DNA can also be reduced.

The double strand-specific DNA degrading enzyme used in the present invention can be preferably an enzyme, which has an activity of cleaving the DNA strand of an RNA-DNA hybrid, and substantially does not have an activity of cleaving the RNA strand of an RNA-DNA hybrid, single-stranded DNA and single-stranded RNA. The double strand-specific DNA degrading enzyme is preferably an enzyme having a DNA-degrading activity even at a temperature of lower than 60° C.

As such double strand-specific DNA degrading enzyme, enzymes derived from prokaryotes or eukaryotes can be used. Preferably, a Crustacea-derived double strand-specific DNA degrading enzyme or a variant thereof can be used.

As such double strand-specific DNA degrading enzyme (which is also referred to as "double strand-specific nuclease (DSN)"), the following enzymes have been known so far (JP Patent Publication (Kokai) 2014-103867 A).
(1) *Solenocera melantho* (coastal mud shrimp) DNase
(2) *Penaeus japonicus* (prawn) DNase
(3) *Paralithodes camtschaticus* (king crab) DSN
(4) *Pandalus borealis* (Northern shrimp) dsDNase
(5) *Chionoecetes opilio* (snow crab) DSN
(6) Other DSN homologs Among the above-described enzymes, king crab DSN and snow crab DSN have heat resistance at an optimum active temperature of about 60° C., whereas Northern shrimp dsDNase is a heat-labile enzyme having an optimum temperature of 37° C.

In the present invention, a shrimp-derived double strand-specific DNA degrading enzyme or a variant thereof is further preferable.

In the present description, the term "variant" is used to mean an enzyme obtained by modifying the amino acid sequence of a natural product-derived double strand-specific DNA degrading enzyme. Specifically, such a variant means an enzyme consisting of an amino acid sequence having sequence identity of 80% or more (preferably 90% or more, and more preferably 95% or more) to the amino acid sequence of a natural product-derived double strand-specific DNA degrading enzyme, and having a double strand-specific DNA-degrading activity, and also, an enzyme consisting of an amino acid sequence comprising a deletion, substitution and/or addition of one or several amino acids (for example, 1 to 10, preferably 1 to 5, and more preferably 1 to 3 amino acids) with respect to the amino acid sequence of a natural product-derived double strand-specific DNA degrading enzyme, and having a double strand-specific DNA-degrading activity.

As a double strand-specific DNA degrading enzyme, a commercially available product can be used. Examples of such a commercially available product include dsDNase (ArcticZymes), Hl-dsDNase (ArcticZymes), dsDNase (Thermo scientific), Shrimp DNase, Recombinant (Affymetrix), Atlantis dsDNase (Zymo Research), and Thermolabile Nuclease (Roche).

An example of the non-specific DNA degrading enzyme used in the present invention is an enzyme, which has an activity of cleaving the DNA strand of an RNA-DNA hybrid and substantially does not have an activity of cleaving the RNA strand of an RNA-DNA hybrid and single-stranded RNA, wherein the activity of cleaving the single-stranded DNA is preferably lower than the activity of cleaving the DNA strand of the RNA-DNA hybrid. The non-specific DNA degrading enzyme is preferably an enzyme having a DNA-degrading activity even at a temperature of lower than 60° C.

As such a non-specific DNA degrading enzyme, an enzyme derived from prokaryotes or eukaryotes can be used. Preferably, a mammal-derived non-specific DNA degrading enzyme or a variant thereof can be used.

In the present invention, a bovine-derived non-specific DNA degrading enzyme or a variant thereof is more preferable.

In the present description, the term "variant" is used to mean an enzyme obtained by modifying the amino acid sequence of a natural product-derived non-specific DNA degrading enzyme. Specifically, the variant means an enzyme consisting of an amino acid sequence having a sequence identity of 80% or more (preferably 90% or more, and more preferably 95% or more) to the amino acid sequence of a natural product-derived non-specific DNA degrading enzyme, and having a non-specific DNA-degrading activity, and also, an enzyme consisting of an amino acid sequence comprising a deletion, substitution and/or addition of one or several amino acids (for example, 1 to 10, preferably 1 to 5, and more preferably 1 to 3 amino acids) with respect to the amino acid sequence of a natural product-derived non-specific DNA degrading enzyme, and having a non-specific DNA-degrading activity.

The primer used in the present invention is composed of a deoxynucleotide and/or a ribonucleotide, and the present primer has a chain length capable of undergoing base pairing with a target nucleic acid under given conditions. The chain length of such a primer is not particularly limited, and it is preferably 5 to 50 nucleotides, and more preferably 5 to 30 nucleotides. As such primers, one or more of types of random primers, oligo dT primers or sequence-specific primers can be preferably used. In the case of using a random primer, the length of the primer is preferably approximately 5 to 10 nucleotides, and more preferably approximately 6 to 8 nucleotides. In the case of using an oligo dT primer, the length of the primer is preferably 10 to 50 nucleotides, and more preferably 15 to 30 nucleotides. In the case of using a sequence-specific primer, the length of the primer is preferably 5 to 30 nucleotides, and more preferably 7 to 20 nucleotides.

The primer can be synthesized by any given method that can be used in the synthesis of an oligonucleotide, such as a phosphite triester method, an H-phosphonate method, or a thiophosphonate method. The primer according to the present invention can be synthesized, for example, by a phosphoramidite method, using DNA Synthesizer Type 394 manufactured by ABI (Applied Biosystem Inc.).

Preferably, a primer, the Tm value of which has been increased by modification with a cation unit, can be used. For example, a Zip Nucleic Acid (ZNA) primer can be used. ZNA has an action to increase the Tm value of an oligonucleotide, using a cation unit (Non Patent Literatures 14 to 16). By using a primer, the Tm value of which has been increased by modification with a cation unit, such as a ZNA primer, amplification efficiency can be enhanced. In particular, by using a random hexamer primer modified with ZNA, the primer can be annealed to template RNA even at a reaction temperature during reverse transcription, and thereby, more efficient strand displacement amplification can be carried out.

The term "substrate" is used in the present description to mean a substrate of RNase H minus reverse transcriptase, and as such a substrate, a mixture of four types of deoxyribonucleotides (dATP, dCTP, dGTP, and dTTP) can be used. However, the substrate is not limited to the mixture of dATP, dCTP, dGTP, and dTTP, and dideoxynucleotide triphosphate may be added to the mixture, or a modified deoxyribonucleotide may also be used.

In the present invention, the mixture to be used in the reaction may comprise a single-stranded DNA-binding protein such as a T4 gene 32 protein. The T4 gene 32 protein can be used as an auxiliary factor for increasing the uniformity of amplification. The T4 gene 32 protein as a single-stranded DNA-binding protein has been known to act, not only on single-stranded DNA, but also on RNA (Non Patent Literatures 17 to 20). By using the T4 gene 32 protein, the higher structure of template RNA can be loosened, and a more uniform strand displacement reaction can be carried out on the full-length template. Moreover, in the case of a reaction using a non-specific DNA degrading enzyme, decomposition of amplified cDNA can be prevented.

The nucleic acid amplification reaction according to the present invention may be carried out under isothermal conditions, or under thermal cycling conditions.

When the nucleic acid amplification reaction is carried out under isothermal conditions, the reaction can be carried out, for example, at a predetermined temperature between 25° C. and 50° C., preferably at a predetermined temperature between 30° C. and 45° C., and more preferably at a predetermined temperature between 35° C. and 40° C., and thus, the reaction can be carried out, for example, at 37° C. for a predetermined period of time (for example, within 5 minutes to 3 hours, and preferably 10 minutes to 150 minutes). When the reaction is carried out, for example, at 37° C., after the reaction solution has been incubated, for example, at 25° C. for a predetermined period of time (for example, 5 minutes to 15 minutes), and then, has been incubated at 30° C. for a predetermined period of time (for example, 5 minutes to 15 minutes), the reaction is carried out at 37° C. Alternatively, after the reaction solution has been incubated at 37° C., it may be incubated at 50° C. for a predetermined period of time (for example, 5 minutes to 15 minutes), and then at 85° C. for a predetermined period of time (for example, 5 minutes to 15 minutes).

When the nucleic acid amplification reaction is carried out under thermal cycling conditions, for example, a predetermined temperature T1 of 20° C. or higher and lower than 30° C. (for example, 25° C.) is combined with a predetermined temperature T2 of 30° C. or higher and 45° C. or lower (for example, 37° C.). Then, T1 for a predetermined period of time (for example, 1 minute to 3 minutes, and as an example, 2 minutes) and T2 for a predetermined period of time (for example, 1 minute to 3 minutes, and as an example, 2 minutes) are set at one cycle, and this cycle is repeated preferably for 10 cycles to 40 cycles, and more preferably for 15 cycles to 35 cycles, so that the reaction can be carried out. In addition, prior to the above-described thermal cycling, the reaction solution may be incubated, for example, at 25° C. for a predetermined period of time (for example, 5 minutes to 15 minutes), then at 30° C. for a predetermined period of time (for example, 5 minutes to 15 minutes), and then at 37° C. for a predetermined period of time (for example, 1 minute to 5 minutes). Moreover, after completion of the above-described thermal cycling, the reaction solution may be incubated at 50° C. for a predetermined period of time (for example, 5 minutes to 15 minutes), and then at 85° C. for a predetermined period of time (for example, 5 minutes to 15 minutes).

The method for amplifying a nucleic acid according to the present invention can be used as a part of an RT-qPCR method of using a trace amount of RNA (for example, trace RNA corresponding to a volume ranging from a single cell to several hundreds of cells).

The method for amplifying a nucleic acid according to the present invention can be utilized in an RNA sequence method of using a trace amount of RNA (for example, trace RNA corresponding to a volume ranging from a single cell to several hundreds of cells).

By utilizing the method for amplifying a nucleic acid according to the present invention, it is possible to detect a single cell in a large amount of cells. Specifically, by specifically amplifying genes expressing only in target cells contained in a large amount of cells, it becomes possible to detect only a few target cell genes contained in a large amount of RNA, so that the presence or absence of target cells can be judged.

The present invention further relates to a kit for carrying out the above-described method for amplifying a nucleic acid according to the present invention. The kit of the present invention comprises, at least, a DNA strand-specific RNA-DNA hybrid strand degrading enzyme such as a double strand-specific DNA degrading enzyme or a non-specific DNA degrading enzyme, and an RNase H minus reverse transcriptase. Preferably, the kit of the present invention further comprises a single-stranded DNA-binding protein (for example, a T4 gene 32 protein). The kit of the present invention may further comprise, as desired, other reagents necessary for carrying out the nucleic acid amplification reaction, a buffer, and the like. Examples of such other reagents include a primer, and deoxyribonucleotide triphosphate.

The present invention will be described in more detail in the following examples. However, these examples are not intended to limit the scope of the present invention.

EXAMPLES

The RT-RamDA method is a method for amplifying a nucleic acid, which comprises a step of incubating a mixture comprising template RNA, a primer, a degrading enzyme specific to DNA in RNA-DNA hybrid such as a double strand-specific DNA degrading enzyme or a non-specific DNA degrading enzyme, an RNase H minus reverse transcriptase, and a substrate. In the RT-RamDA method, the complementary strand DNA (cDNA) of template RNA is synthesized by the RNA-dependent DNA polymerase activity of the RNase H minus reverse transcriptase, the cDNA strand in the RNA-cDNA hybrid is randomly cleaved with the degrading enzyme specific to DNA in RNA-DNA hybrid. The above described cleavage site becomes a starting point, the cDNA strand on the 3' side is peeled from RNA by the strand displacement activity of the RNase H minus reverse transcriptase, and a novel cDNA strand is synthesized in the portion peeled by the RNase H minus reverse transcriptase.

RamDA-A is an aspect of carrying out the RT-RamDA method, using a double strand-specific DNA degrading enzyme and a T4 gene 32 protein.

RamDA-B is an aspect of carrying out the RT-RamDA method, using a double strand-specific DNA degrading enzyme, without using a T4 gene 32 protein.

RamDA-C is an RT-RamDA thermal cycling method, which is an aspect of performing a reaction by modifying reaction temperature conditions, while maintaining the same composition of the reaction solution as that in RamDA-B, and by repeating with short intervals an annealing step and an elongation reaction step.

RamDA-D is an aspect of carrying out the RT-RamDA method, using a non-specific DNA degrading enzyme and a T4 gene 32 protein.

(Materials and Methods)
Cell Culture

For extraction of total RNA, 5G6GR mouse ES cells were used. This cell line was produced by randomly incorporating a linearized Gata6-GR-IRES-Puro vector into EB5 ES cells (Non Patent Literature 20). The cells were cultured on a feeder-free gelatin-coated dish, in a 10% fetal bovine serum-containing Glasgow minimal essential medium (GMEM; Sigma-Aldrich, St Louis, Mo., USA) comprising 1000 U/ml leukemia inhibitory factor (ESGRO; Invitrogen Corp., Carlsbad, Calif., USA), 100 μmol/l 2-mercaptoethanol (Nacalai Tesque Inc., Kyoto, Japan), 1× non-essential amino acids (Life Technologies Corp., Carlsbad, Calif., USA), 1 mmol/1 sodium pyruvate (Life Technologies), 2 mmol/l L-glutamine (Nacalai Tesque), 0.5× penicillin/streptomycin (Life Technologies), and 10 μg/ml blasticidin (Life Technologies).

RNA Extraction

Total RNA was purified using RNeasy Mini Kit (Qiagen Inc., Valencia, Calif., USA). Quantification of RNA and the quality check thereof were carried out using Quantus Fluorometer (Promega Corp., Madison, Wis., USA) and RNA 6000 Nano Kit (Agilent Biotechnology, Santa Clara, Calif., USA). Artificially synthesized RNA was synthesized from pGIBS-DAP, pGIBS-THR plasmid (American Type Culture Collection (ATCC), Manassas, Va., USA), using MEGAscript T3 kit (Life Technologies).

Preparation of 1-Cell Lysate of Mouse ES Cells

The cultured cells were reacted at 37° C. for 3 minutes, using TrypLE Express (Life Technologies), so as to dissociate the cells into 1 cell. After completion of the dissociation, the reagent was immediately replaced with PBS (−) to terminate the reaction. In order to precisely fractionate only the cell using a cell sorter, the living cell nucleus of the dissociated cell was labeled by staining it using Vybrant Dye Cycle (Life Technologies). The method included in the reagent was applied as staining conditions. Using SH 800 Cell Sorter (Sony Corp., Tokyo, Japan), cells, which showed positive to Vybrant Dye Cycle (detection filter: BP450/50) and showed negative to dead cell fluorescence marker dye, PI (detection filter: BP585/40), were defined as a living cell fraction. From this fraction, 50 cells were fractionated into 1 μl of Lysis buffer (1 U of RNasein plus (Promega), 0.3% NP40 (Thermo Fisher Scientific Inc., Waltham, Mass. USA), and RNase free water (TaKaRa Bio Inc., Otsu, Japan)). After completion of the fractionation, the cells were immediately subjected to spinning down and stirring by shaking, and the resulting cells were then conserved at −80° C. When the cells were used in a reverse transcription reaction, the cells were thawn, and 49 μl of Lysis buffer was then added to the resulting cells, so that 1 μl of 50-fold diluted cell lysate was used as a 1-cell lysate.

FRET Assay

FRET analysis was carried out by modifying the method of Inge W. Nilsen et al (Non Patent Literature 12). 0.6 μl of oligonucleotide probe mix (6 pmol of oligo DNA or RNA (Sigma-Aldrich), 1× First-Strand buffer (Life Technologies), and RNase free water (TaKaRa)) was prepared, and was then denatured at 70° C. for 5 minutes. Thereafter, the temperature was slowly returned to room temperature. Combinations of oligonucleotides used in the analysis are as follows (SEQ ID NOS: 1 to 10).

```
Dual probe for double-stranded DNA:
FAM-CGCCATCGGAGGTTC-BHQ1

HEX-GAACCTCCGATGGCG-BHQ1

Dual probe for RNA-DNA hybrid:
FAM-CGCCATCGGAGGTTC-BHQ1

HEX-rGrArArCrCrUrCrCrGrArUrGrGrCrG-BHQ1
```

```
Single probe for single-stranded DNA:
HEX-GAACCTCCGATGGCG-BHQ1

Single probe for single-stranded RNA:
HEX-rGrArArCrCrUrCrCrGrArUrGrGrCrG-BHQ1

Single FAM probe for correction:
FAM-CGCCATCGGAGGTTC-BHQ1

GAACCTCCGATGGCG

Single HEX probe for correction:
CGCCATCGGAGGTTC

HEX-GAACCTCCGATGGCG-BHQ1
```

Subsequently, 5.4 μl of enzyme solution (1× First-Strand buffer, 0.12 U of each nuclease, and RNase free water) was prepared. As nucleases, DNase I Amplification Grade (Life Technologies), dsDNase (ArcticZymes AS, Tromso, Norway), and HL-dsDNase (ArcticZymes) were used. As a control, RNase free water was added instead of the enzyme. 0.6 μl of the oligonucleotide probe mix, which had been returned to room temperature, was mixed with 5.4 μl of the enzyme solution on PloxiPlate-384F Plus (PerkinElmer Inc., Waltham, Mass., USA), and the obtained mixture was then measured using EnVision (PerkinElmer). For the measurement, the fluorescence intensities of FAM and HEX were measured at 37° C. at a rate of one measurement for 70 seconds, and this measurement was carried out 50 times. The leakage of the fluorescence of FAM and HEX was corrected using the fluorescence amount of each single probe for correction.

In a verification experiment regarding the action of a T4 gene 32 protein on nuclease activity (FIG. 10), 0.6 μl of oligonucleotide probe mix (6 pmol of oligo DNA or RNA (Sigma-Aldrich), 1× PrimeScript Buffer (for Real Time) (TaKaRa), and RNase free water) and 5.4 μl of enzyme solution (1× PrimeScript Buffer (for Real Time) or 1× DNase I reaction buffer (Life Technologies), 0.12 U of each nuclease, and RNase free water) were prepared. As nucleases, DNase I Amplification Grade and dsDNase were used. As a T4 gene 32 protein-added sample, 180 ng of T4 gene 32 protein (Roche Applied Science, Indianapolis, Ind., USA) was added to the enzyme solution. As a control, RNase free water was added instead of the enzyme. The measurement was carried out at a rate of one measurement for 90 seconds, 50 times. The enzyme activity was calculated using the fluorescence amplification rate in the initial stage of reaction (1.5 minutes to 9 minutes).

In a measurement experiment regarding KCl and Tris-HCl concentration-dependent nuclease activity of DNase I (FIG. 6), 0.6 μl of oligonucleotide probe mix (6 pmol of oligo DNA or RNA (Sigma-Aldrich), 1× DNase I reaction buffer (Life Technologies), and RNase free water) and 5.4 μl of enzyme solution (in-house reaction buffer, 0.12 U of DNase I Amplification Grade, and RNase free water) were prepared. The in-house reaction buffer was adjusted to have a final concentration shown in FIG. 6, depending on conditions. The measurement was carried out at a rate of one measurement for 60 seconds, 50 times. The enzyme activity was calculated using the fluorescence amplification rate in the initial stage of reaction (5 minutes to 10 minutes). Combinations of oligonucleotides used in the analysis are as follows (SEQ ID NOS: 11 to 16).

```
Single probe for double-stranded DNA:
FAM-CGCCATCGGAGGTTC-BHQ1

GAACCTCCGATGGCG-BHQ1

Single probe for RNA-DNA hybrid:
FAM-CGCCATCGGAGGTTC-BHQ1 rGrArArCrCrUrCrCrGrArUrGrGrCrG-BHQ1

Single probe for single-stranded DNA:
FAM-CGCCATCGGAGGTTC-BHQ1

Single probe for single-stranded RNA:
FAM-rCrGrCrCrArTrCrGrGrArGrGrTrTrC-BHQ1
```

Reverse Transcription Reaction

RT-RamDA Method (RamDA-A):

Template RNA was diluted with 1 μl of Lysis buffer (1 U of RNasein plus (Promega), 10% Roche lysis buffer (Roche), 0.3% NP40 (Thermo Fisher), and RNase free water), and was then subjected to a denaturation treatment at 65° C. for 2 minutes. The resulting RNA was conserved on ice before use. ReverTra Ace qPCR RT KIT (TOYOBO Co. Ltd., Osaka, Japan) was modified, and was used as a reverse transcriptase the reaction solution. To 1 μl of the denatured diluted template RNA, 2 μl of RT mix (1.5× ReverTra Ace RT buffer (TOYOBO), 0.6 pmol of oligo (dT) 18 primer (Thermo Fisher), 7.8 pmol of random hexamer primer (TaKaRa), 1.5× ReverTra Ace enzyme mix (TOYOBO), and RNase free water), or 2 μl of RamDA-A mix (1.5× ReverTra Ace RT buffer, 0.6 pmol of oligo (dT) 18 primer, 7.8 pmol of ZNA-random hexamer primer ([Z][Z]NNNNNN; Sigma-Aldrich), 0.4 U of dsDNase (ArcticZymes), 100 ng of T4 gene 32 protein, 1.5× ReverTra Ace enzyme mix, and RNase free water) was added. The thus obtained mixtures were each stirred at 2,000 rpm for 30 seconds using MixMate (Eppendorf, Westbury, N.Y., USA), and were then reacted using a thermal cycler C1000 (Bio-Rad Laboratories, Inc., Hercules, Calif., USA)), at 25° C. for 10 minutes, at 30° C. for 10 minutes, at 37° C. for 30 minutes, at 50° C. for 5 minutes, and at 85° C. for 5 minutes.

RT-RamDA Method without Using T4 Gene 32 Protein (RamDA-B):

Template RNA was diluted with 1 μl of lysis buffer (1 U of RNasein plus, 0.3% NP40, and RNase free water), and was then subjected to a denaturation treatment at 70° C. for 90 seconds. The resulting RNA was cooled on ice, and thereafter, 2 μl of RT mix (1.5× ReverTra Ace RT buffer, 0.6 pmol of oligo (dT) 18 primer, 7.8 pmol of random hexamer primer, 1.5× ReverTra Ace enzyme mix, and RNase free water), or 2 μl of RamDA-B mix (1.5× ReverTra Ace RT buffer, 0.6 pmol of oligo (dT) 18 primer, 7.8 pmol of ZNA-random hexamer primer([Z][Z]NNNNNN; Sigma-Aldrich), and 0.1 U of dsDNase) was added. Thereafter, the thus obtained mixtures were each subjected to the same operations as those performed in RamDA-A.

RT-RamDA Thermal Cycling Method (RamDA-C):

A reverse transcription reaction was carried out with the same reaction solution composition as that of RamDA-B, with the exception that the temperature conditions were changed. The reaction conditions are as follows. After a reaction had been carried out at 25° C. for 10 minutes, at 30° C. for 10 minutes, and at 37° C. for 2 minutes, a reaction at 25° C. for 2 minutes, and then at 37° C. for 2 minutes was carried out for 29 cycles. Thereafter, the reaction product was treated at 50° C. for 5 minutes, and then at 85° C. for 5 minutes.

RT-RamDA Non-Specific DNA Degrading Enzyme (DNase I) Method (RamDA-D):

Template RNA was diluted with 1 μl of Lysis buffer (1 U of RNasein plus, 10% Roche lysis buffer, 0.3% NP40, and RNase free water), and was then subjected to a denaturation treatment at 70° C. for 90 seconds. The resulting RNA was conserved on ice before use. PrimeScript RT reagent Kit (Perfect Real Time) (TaKaRa) was modified, and was used as a reverse transcriptase the reaction solution. To 1 μl of the denatured template RNA, 2 μl of RT mix (1.5× PrimeScript Buffer (for Real Time), 0.6 pmol of oligo (dT) 18 primer, 8 pmol of random hexamer primer, 1.5× PrimeScript RT Enzyme Mix I, and RNase free water), or 2 μl of RamDA-D mix (1.5× PrimeScript Buffer (for Real Time), 0.6 pmol of oligo (dT) 18 primer, 8 pmol of random hexamer primer, 0.2 U of DNase I, Amplification Grade, 100 ng of T4 gene 32 protein, 1.5× PrimeScript RT Enzyme Mix I, and RNase free water) was added. The thus obtained mixtures were each reacted at 25° C. for 10 minutes, at 30° C. for 10 minutes, at 37° C. for 60 minutes, at 50° C. for 5 minutes, and at 85° C. for 5 minutes.

Experiment for Studying Composition of Reverse Transcription Reaction Solution, Using RamDA-D:

When a in-house reverse transcription reaction buffer, in which the concentrations of Tris-HCl, KCl, NaCl and MgCl$_2$ were changed, or First-Strand Buffer was used, these were replaced with PrimeScript Buffer (for Real Time) in RamDA-D mix, and dNTP Mix (Life Technologies) was further added to the solution to a final concentration of 0.5 mM, followed by performing the reaction. The composition of each buffer is shown in Table 1 below.

TABLE 1

Compositions of in-house reaction buffers and commercially available enzyme-added reaction buffers
1 X Concentration (mM)

| Buffer | Tris-HCl pH 8.4 | Tris-HCl pH 8.3 | KCl | NaCl | MgCl2 |
|---|---|---|---|---|---|
| FIG. 7-a | 20.0 | | 50.0 | 0.0 | 2.0 |
| FIG. 7-b | 20.0 | | 62.5 | 0.0 | 2.0 |
| FIG. 7-c | 20.0 | | 75.0 | 0.0 | 2.0 |
| FIG. 7-d | 35.0 | | 50.0 | 0.0 | 2.0 |
| FIG. 7-e | 35.0 | | 62.5 | 0.0 | 2.0 |
| FIG. 7-f | 35.0 | | 75.0 | 0.0 | 2.0 |
| FIG. 7-g | 50.0 | | 50.0 | 0.0 | 2.0 |
| FIG. 7-h | 50.0 | | 62.5 | 0.0 | 2.0 |
| FIG. 7-i | 50.0 | | 75.0 | 0.0 | 2.0 |
| FIG. 7-j | | 50.0 | 75.0 | 0.0 | 3.0 |
| FIG. 7-k | | 50.0 | 75.0 | 10.0 | 3.0 |
| FIG. 7-l | | 50.0 | 75.0 | 20.0 | 3.0 |
| DNase I reaction buffer (Life Technologies) | *20.0 | | *50.0 | | *2.0 |
| First-Strand Buffer (Life Technologies) | | *50.0 | *75.0 | | *3.0 |
| PrimeScript Buffer (for Real Time) (TaKaRa) | — | — | — | — | — |

*Catalog value;
—: Unreleased

Artificially Synthesized RNA (Dap and Thr) System of Using RamDA-D:

Only 0.6 pmol of oligo (dT) 18 primer was used as a reverse transcription primer in RamDA-D mix, and the composition of the RamDA-D mix was changed depending on conditions. In addition, the temperature conditions for the reverse transcription reaction were determined to be the same conditions as those for RamDA-A.

Studies Regarding Reverse Transcriptase in RamDA-D:

With regard to SuperScript II, SuperScript III, and SuperScript IV conditions, 30 U of SuperScript II (Life Technologies), 30 U of SuperScript III (Life Technologies), and 30 U of SuperScript IV (Life Technologies) were used as reverse transcriptase in RamDA-D mix, instead of PrimeScript RT Enzyme Mix I, and further, 6 U of RNasein plus were also added. As a reverse transcription reaction buffer, PrimeScript Buffer (for Real Time) was used for all conditions.

Comparison of dsDNase:

Nuclease was replaced with 0.2 U of 43 KDa dsDNase (ArcticZymes), 0.2 U of 47 KDa dsDNase (Affymetrix Inc., Santa Clara, Calif., USA), and 0.2 U of duplex specific nuclease (DSN; Evrogen JSC, Moscow, Russia), respectively, under the RamDA-A reaction solution conditions, and a comparison was then made. The reaction temperature conditions were determined in accordance with RamDA-A, and the amplification rate of cDNA was then quantified by qPCR.

Comparison of Reverse Transcriptase:

A comparison was made using 10 types of qPCR RT kits, Maxima H Minus First Strand cDNA Synthesis Kit (Thermo Fisher), ReverTra Ace qPCR RT Kit (TOYOBO), PrimeScript RT reagent Kit (TaKaRa), AffinityScript QPCR cDNA Synthesis Kit (Agilent Biotechnology), QuantiTect Rev. Transcription Kit (Qiagen), GoScript Reverse Transcription System (Promega), iScript Select cDNA Synthesis Kit (Bio-Rad), ProtoScript II First Strand cDNA Synthesis Kit (New England Biolabs, MA, UK), SuperScript III (Life Technologies), and Transcriptor First Strand cDNA Synthesis Kit (Roche).

For an elongation activity test, a reverse transcription reaction was carried out using Millennium RNA Markers (Life Technologies) comprising poly-A-added RNAs with various lengths (0.5-9 k bases). A reverse transcription mixture was prepared using reagents supplied to each kit, applying the conditions for formulation of the reagents recommended by the kit, in 10 μl of a reaction system. However, as a reverse transcription primer, an oligo (dT) 18 primer was used in all of the kits. 1.5 μl of RNA-primer mix (20 ng of Millennium RNA Markers, 25 pmol of oligo (dT) 18 primer, and lysis buffer (RamDA-A conditions)) was denatured at 65° C. for 2 minutes, it was then mixed with 8.5 μl of reverse transcription mix, and the obtained mixture was then reacted at 42° C. for 2.5 minutes, and then at 85° C. for 5 minutes. After completion of the reaction, the reaction mixture was analyzed by agarose gel electrophoresis.

For an adaptation test of the RamDA method, using 10 pg of total RNA derived from mouse ES cells, a reverse transcription reaction was carried out. For the preparation of a reverse transcription mixture, reagents supplied to each kit were used, and for formulation of the reagents, 3 μl of a reaction system, which was down-scaled under conditions recommended by the kit, was used. However, regarding reverse transcription primers, 0.6 pmol of oligo (dT) 18 primer and 7.8 pmol of random hexamer primer were used under RamDA (−) conditions, whereas 0.6 pmol of oligo (dT) 18 primer and 7.8 pmol of ZNA-random hexamer primer were used under RamDA (+) conditions. Moreover, in the case of RamDA (+), 0.2 U of dsDNase (ArcticZymes) and 100 ng of T4 gene 32 protein were further added. The reaction was carried out under reaction temperature conditions of 25° C., 10 minutes, 30° C., 10 minutes, 42° C., 30 minutes, 50° C., 5 minutes, and 85° C., 5 minutes, and the amplification rate of cDNA was then quantified by qPCR.

Preparation of reagents and the reactions were all carried out on 0.2 ml of Hi-Tube Flat Cap Recovery (TaKaRa), EU Semi-domed 8-cap strip (BIOplastics BV, Landgraaf, Netherlands), or RP, LF, SEMI Sk, cutable, 96 well plate (BIOplastics BV).

Quantitative Polymerase Chain Reaction (qPCR)

In the case of an artificially synthesized RNA (Dap and Thr) system, a reverse transcription reaction product was diluted with nuclease free water (Qiagen), and the diluted product in an amount of 1/50 was used as a qPCR reaction solution. In the case of a system of 10 pg of Total RNA derived from mouse ES cells, a reverse transcription reaction product was diluted with nuclease free water, and the diluted product in an amount of 1/6, 1/8, or 1/10, was used as a qPCR reaction solution. The qPCR was carried out using LightCyclar 480 (Roche) or ABI 7900HT (Life Technologies) under the following conditions. 10 µl of qPCR reaction solution (1× Quantitect SybrGreen master mix (Qiagen), 5 pmol of forward primer, 5 pmol of reverse primer, 3 µl of diluted cDNA, and nuclease free water) was reacted at 95° C. for 15 minutes to activate the enzyme, and thereafter, denaturation at 95° C. for 15 seconds and an elongation reaction at 60° C. for 1 minute were carried out for 40 cycles. The melting curve was analyzed at 95° C. for 15 seconds, at 60° C. for 15 seconds, and at 95° C. for 15 seconds. For the production of standard curves used for absolute quantification, as standard DNAs, 5-fold dilution series of a dsDNA mixed solution of Dap and Thr (31250, 6250, 1250, 250, 50, 10, and 0 copy) were used for artificially synthesized RNA, and 5-fold dilution series of mouse genomic DNA (Clonetech) (31250, 6250, 1250, 250, 50, 10, and 0 copy) were used for total RNA. Since cDNA was ssDNA, the quantitative value was calculated by the formula: a detected value (dsDNA copy)×2. The sequences of individual primers are shown in Table 2. Data analysis was carried out using LightCycler 480 Software, Version 1.5 (Roche) or SDS Software 2.1 (Life Technologies).

TABLE 2

Primer sequence (SEQ ID NOS: 17 to 80)

| Accession No. | Name of primer | Forward primer sequence (5' → 3') | Reverse primer sequence (5' → 3') | Position from 3' end (nt) |
|---|---|---|---|---|
| NM_008143 | Gnb2l1 | TGACCAGAGATGAGACCAACTATGG | AAGTGGGAGTGACCTCTCAGAGC | 1016 |
| NM_028016 | Nanog | TGATTCTTCTACCAGTCCCAAACAA | TGAGAGAACACAGTCCGCATCTT | 1807 |
| NM_013633 | Oct3/4 | CCCGGAAGAGAAAGCGAACT | CGGGCACTTCAGAAACATGG | 620 |
| NM_011443 | Sox2 | TCTTGCTGGGTTTTGATTCTGC | CAAATCCGAATAAACTCCTTCCTTG | 543 |
| NM_009556 | Rex1 | CTCAAGCCGGGTGCAAGA | GCCCGTGGACAAGCATGT | 893 |
| NM_018796 | Eef1b2 | CCTTCGCCATGGGATTCG | CGCCAGGTAATCGTTGAGCA | 1619 |
| NM_007505 | Atp5a1 | GTACCCTCCTTCCACCGGG | GCCATTGCTGAGGTCACACAG | 289 |
| NM_011655 | Tubb5 | CAGTCTGAGACCGGCCCAG | TGTGCACGATTTCCCTCATG | 2505 |
| | Dap_1856 | AAATTAGTCATTGCGGGACCG | TCGTTCTGCCAATTTAACAGCTTC | 1856 |
| | Dap_1795 | GAACACCACATTTTGACCTTGTAGG | GAAAGCATCTGACTCAACAGGCA | 1797 |
| | Dap_1653 | GATTGATTTAACAACGCCGAA | TCCGTGCTCTAATGCAATTTTTG | 1653 |
| | Dap_1334 | GAAAAGCAGCAAGGACATCCG | TGCTCCGCTCCTCTTGCTC | 1334 |
| | Dap_1209 | GTCAGGCGTTAAACTGTCAGTCG | TTTATCCCCCCGTCTAATCAATG | 1209 |
| | Dap_962 | TTTCAATCCGGCCCTTTAGG | AGTGCATTGGCAGCGATCAG | 962 |
| | Dap_785 | ACTGCGGAAATTCTTGTGCG | CGAAGAAGGTCACGGAATTCG | 785 |
| | Dap_686 | TTTTGGCGCCCACAGTGAT | GACAAACTTCGCTATTGTGCCG | 686 |
| | Dap_539 | AGCTGAAGCAGCCCGCATA | GCGGTCTGGAAGCGTTAGC | 539 |
| | Dap_367 | AATGCGGCTGCACTGGTG | CGTCTTTATATTTATGATTCCGGC | 367 |
| | Dap_152 | TTCCGTTTCTACTCCTCTGACGAA | GGCATACTCCACGCCCG | 152 |
| | Dap_86 | TAAAGAAGCGGGCGTGGAGTA | TTTGGATCCTCAGCATCCGTT | 86 |
| | Thr_2022 | CTCGAGATGTGGAAAGGACTTATCC | CATGTAAAGTTAGCGCCGGTGT | 2022 |
| | Thr_1831 | AATGGTTATGGCTGTGGCAAAG | CAGCAGCGGAAGTGTTACCTG | 1831 |
| | Thr_1606 | AATTGTCCGTTCCATCTGTGAGA | GTAAGGGTTGACTGAGTTGACAAGG | 1606 |
| | Thr_1411 | GAAAAACGGCACAGGCCTTC | CGATTGCCCCCGCAC | 1411 |
| | Thr_1065 | CTGAAAGATCCGAACACAGCG | TCAGTCGGCAATGTGACAGG | 1065 |

TABLE 2-continued

Primer sequence
(SEQ ID NOS: 17 to 80)

| Accession No. | Name of primer | Forward primer sequence (5' → 3') | Reverse primer sequence (5' → 3') | Position from 3' end (nt) |
|---|---|---|---|---|
| | Thr_858 | AGCTGACCG TCTTTGAAA GCG | TTCCGGCGA CTGTTTCTG TTT | 858 |
| | Thr_767 | AGTGGCTAA ACGGACCGC A | CACCTTCAC ATGGACAGG AGG | 767 |
| | Thr_613 | ATGCTGGCG CTTCTCTCG T | TGGGTCTCG TCATCCTCA TG | 613 |
| | Thr_544 | CTCGTCGGC GGACTTGTG | GGACGCGGA TCATTTGGG | 544 |
| | Thr_439 | GTGCTGACA AGAGACGCG AGA | TTTACGGCA TCGGCATAT GG | 439 |
| | Thr_295 | ATGTTCCAT CAGCCGTAC CG | GGCGACGTG CTCTACTTT TGA | 295 |
| | Thr_200 | CGGAGCAGG CCCAACG | GGGAAATGA AGCGCGAGC | 200 |

Gel Electrophoresis

Each reverse transcription reaction product was diluted with an RNase-free TE buffer (Life Technologies) to result in a volume of 20 µl, and the thus diluted product was subjected to a denaturation treatment at 70° C. for 10 minutes, and immediately after the treatment, the reaction solution was cooled on ice. Regarding DNA ladder markers, 1 µl of E-Gel 1 Kb Plus DNA Ladder (Life Technologies), which was diluted with an RNase-free TE buffer to a volume of 20 µl and was then thermally denatured, was used as an ssDNA ladder, and 1 µl of E-Gel 1 Kb Plus DNA Ladder (Life Technologies) which was diluted but was not thermally denatured, was used as a dsDNA ladder. However, in a system of using Millennium RNA Markers, a thermal denaturation treatment was omitted after completion of the dilution. The reverse transcription reaction product and the ladder marker were filled into 2% E-Gel EX Agarose Gels (Life Technologies), and thereafter, electrophoresis was carried out using E-Gel iBase Power System (Life Technologies) for 10 minutes. Electrophoretic images were photographed using FAS-Digi (NIPPON Genetics Co. Ltd, Tokyo, Japan).

(Results)
Selective Cleavage of DNA in RNA-DNA Hybrid by dsDNase and DNase I

First, whether dsDNase or DNase I has an activity of selectively cleaving DNA in an RNA-DNA hybrid under standard reserve transcription buffer conditions was examined.

Crab-derived double strand-specific nuclease has been known to have an activity of cleaving DNA in an RNA-DNA hybrid (Non Patent Literature 11). However, this enzyme has almost no activity at a temperature applied during reverse transcription (Non Patent Literature 11). As such, shrimp-derived dsDNase known as a thermally unstable enzyme has been focused (Non Patent Literature 12). This enzyme has an activity around 37° C. and specifically cleaves double-stranded DNA. Thus, this enzyme has an action to remove contaminated DNA, genomic DNA and the like without digesting primers or cDNA (Non Patent Literatures 12 and 13). However, it had not yet been reported that this enzyme has an activity of cleaving DNA in an RNA-DNA hybrid, which is essential for carrying out a strand displacement reaction. Hence, using Fluorescence resonance energy transfer (FRET), an analysis was carried out. As a result, it was found that dsDNase has an activity of selectively cleaving the DNA in an RNA-DNA hybrid, although the activity is about a half of the activity on double-stranded DNA (FIGS. 2A to 2C). In addition, it was also confirmed that this enzyme has almost no activity on an RNA strand in an RNA-DNA hybrid, single-stranded DNA, and single-stranded RNA (FIGS. 2D to 2F). Similar results were obtained from heat-labile double-strand specific DNase (HL-dsDNase) having higher thermal instability than the dsDNase, but it was found that the nuclease activity of HL-dsDNase is lower than that of dsDNase (FIGS. 2A to 2C). On the other hand, when DNase I as a non-specific DNase was used, it exhibited an activity of selectively cleaving DNA in an RNA-DNA hybrid, as with dsDNase. However, this enzyme also exhibited an activity on single-stranded DNA, although the activity was low (FIGS. 2B and 2E). In view of foregoing, first, an RT-RamDA method of using dsDNase that does not exhibit degradation activity on single-stranded DNA was examined.

Amplification by Fragmentation of cDNA and Strand Displacement Reaction

In order to confirm whether dsDNase actually acts on cDNA synthesized by a reverse transcription reaction so as to fragment it, and also, whether a strand displacement reaction thereby takes place and cDNA is amplified, reverse transcription was carried out using about 2 kb of poly-A-added artificially synthesized RNA as a template, and thereafter, the presence or absence of fragmentation of cDNA was examined by gel electrophoresis, and the yield of cDNA was measured by RT-qPCR. Consequently, it was found that, in a standard reverse transcription method (RamDA (−)), almost no fragmentation took place in both cases of an oligo dT primer and a random hexamer primer. On the other hand, in RamDA (+), cDNA was fragmented, and a smear electrophoretic image was obtained (FIG. 3A). It was suggested that these results should be obtained by the action of dsDNase to cleave the cDNA in an RNA-cDNA hybrid. Subsequently, in order to quantitatively detect amplification caused by a strand displacement reaction, absolute quantification of cDNA was carried out by qPCR. As template RNA, artificially synthesized RNAs, Dap (1,910 b) and Thr (2,052 b), were each mixed in an amount of 100 fg each (Dap: 96,725 copies, Thr: 89,991 copies) with 10 pg of total RNA derived from mouse ES cells (corresponding to a single cell), and the mixture was then used to carry out a reverse transcription. Quantification was carried out according to qPCR, by designing qPCR primers in 12 regions from the 3'-end to the 5'-end in each artificially synthesized RNA, and measuring the detected amount in each region. As a result, in both cases of Dap and Thr, an almost constant detected amount was shown in all of the regions either under the oligo dT primer conditions or under the random hexamer primer conditions, under RamDA (−) control conditions (FIG. 3B). On the other hand, in the case of RamDA (+), not only under conditions of using the random hexamer primer, but also under conditions of using the oligo dT primer, in regions 500 nt or more from the 3' side, the detected amount of cDNA was stably increased to nearly 10 times that of the RamDA (−) control (FIG. 3B). Moreover, it was found that the increased amount was relatively low around the 3'-end (FIG. 3B). From these results, it was suggested that an increase in the amount of cDNA detected in RamDA (+) should be amplification by a strand displacement reaction, and that the nick on the cDNA side formed by dsDNase would become a starting point of the strand displacement reaction.

dsDNase Enzyme and Reverse Transcriptase that can be Used in RT-RamDA Method

In order to examine a dsDNase enzyme and reverse transcriptase that can be used in an RT-RamDA method, whether amplification effects can be obtained even under conditions of using other dsDNase enzymes or various types of reverse transcriptases was examined. First, regarding dsDNase enzymes, a comparison was made among three enzymes, namely, dsDNase (43 KDa) commercially available from ArcticZymes, dsDNase (47 KDa) of Affymetrix, and duplex specific nuclease (DSN) of Evrogen. Using 10 pg of total RNA derived from mouse ES cells that was the amount of total RNA corresponding to a single cell, reverse transcription was carried out. As a result, a significant increase in the detected amount of cDNA was observed in the two dsDNase-added samples (FIG. 4A). The amplification rate of DSN was very low because of a difference in active temperature, but it was found that if the enzyme is a double strand-specific DNase, the type of the double strand-specific DNase is not particularly limited to a specific enzyme.

Next, the presence or absence of amplification effects obtained by the RT-RamDA method was examined using commercially available reverse transcriptase. First, to examine the elongation activity of an enzyme, poly-A-added Millennium RNA Markers (Life Technologies) were used to perform reverse transcription using an oligo dT primer, so that a performance test was carried out. As a result, it was found that, regardless of a short elongation time that was 2 minutes 30 seconds, almost all enzymes had an elongation activity of 2 kb or more (FIG. 4B). Moreover, reverse transcriptases, which did not have an RNase H activity, showed a clear ladder pattern (FIG. 4B, a-c, h, and i), whereas reverse transcriptases having an RNase H activity showed a dark smear pattern (FIG. 4B, e-g and j). When SYBR Gold (Life Technologies) used as a DNA-staining dye is reacted with single-stranded DNA, it provides fluorescence intensity that is about a half in the case of reacting with double-stranded DNA (Non Patent Literature 22). Thereby, it is assumed that a difference in the electrophoretic patterns indicates the presence or absence of an RNA-DNA hybrid strand.

Next, individual reverse transcriptases were used to perform reverse transcription using 10 pg of total RNA derived from mouse ES cells, under conditions of addition (+) of RT-RamDA components (dsDNase, a T4 gene 32 protein, and a ZNA-random hexamer primer), or non-addition (−) of such components, and a comparison was then made by qPCR, in terms of the yield of cDNA. As a result, in all of reverse transcriptases having no RNase H activity, in the case of RamDA (+), an increase in the detected amount was observed (FIG. 4C, a-c, h, and i). On the other hand, in reverse transcriptases having RNase H activity, such an increase in the detected amount was not observed, or the detected amount was decreased (FIG. 4C, e-g and j). Moreover, although RNase H activity was not referred to nominally, AffinityScript also exhibited slight amplification in RamDA (+) (FIG. 4B, d). However, since AffinityScript showed a smear pattern in its electrophoretic image, it was assumed that it had an RNase H activity although the activity was weak (FIG. 4B, d). From these results, it was found that the amplification action of the RT-RamDA method is not limited to specific dsDNase or specific reverse transcriptase, but that this is a widely used technique as long as the enzymes are dsDNases having an activity around 37° C. and reverse transcriptases having no RNase H activity. Furthermore, if an enzyme had an RNase H activity, it did not show amplification effects. Accordingly, it was demonstrated that strand displacement amplification takes place, directly using RNA as a template.

Concerning Method of Enhancing Reaction Efficiency of RT-RamDA Method

The present inventors have focused on the improvement of an amplification rate, and have developed deviation methods, namely, an RT-RamDA method (RamDA-B) without using a T4 gene 32 protein and an RT-RamDA thermal cycling method (RamDA-C). In a strand displacement reaction, formation of the secondary structure of a template hinders amplification. The present inventors have introduced a T4 gene 32 protein into the RT-RamDA method (RamDA-A) as a role for alleviating such a secondary structure. However, at the same time, it was assumed that the T4 gene 32 protein would cause instabilization of a DNA-RNA hybrid, and would suppress the activity of dsDNase. As such, RamDA-B without using such a T4 gene 32 protein was attempted. Using 10 pg of total RNA derived from mouse ES cells as a template, the synthesis of cDNA was carried out. As a result, it was found that, under the conditions of RamDA-B, the detected amounts of Gnb2l1 and Oct3/4 were increased to 40 times or more, in comparison to a standard reverse transcription method (RamDA (−)) (FIG. 5A). On the other hand, regarding Nanog, Sox2, Eef1b2 and the like, a great difference was not found between RamDA-B and RamDA-A (FIG. 5A).

Next, RamDA-C, in which only the reaction temperature conditions in RamDA-B were modified and an annealing step and an elongation were repeated with short intervals, was attempted. As a result, it was found that the detected amounts of Gnb2l1 and Oct3/4 in RamDA-C were increased to 100 times or more those in a standard reverse transcription method (FIG. 5B, RamDA (+) cycle). On the other hand, in the standard reverse transcription method, the effects of thermal cycling were not observed (FIG. 5B, RamDA (−) cycle). In addition, in RamDA-A as well, the effects of thermal cycling were not observed (the data is not shown). From these results, it was suggested that, in the RamDA-B method, the re-annealing of a primer should be extremely effective for amplification of cDNA. In particular, the ZNA-random hexamer primer involves addition of two cation units, and the Tm value of the ZNA-random hexamer primer has been designed to be approximately 26° C. higher than that of a general random hexamer primer (Non Patent Literature 14). Thus, the ZNA-random hexamer primer enables efficient annealing even during a reaction at 37° C., and further, it is considered that annealing has been further promoted by thermal cycling.

Concerning RT-RamDA Method of Using DNase I

The greatest reason for the use of dsDNase in the RT-RamDA method is that the dsDNase does not have a nuclease activity on amplified cDNA that is single-stranded DNA, and a reverse transcription primer. However, it has been known that DNase I that is a non-specific DNA degrading enzyme originally has a lower nuclease activity on single-stranded DNA, than on double-stranded DNA (Non Patent Literature 12), and that its nuclease activity is reduced in a monovalent cation (e.g. K+, Na+, etc.) dependent manner (Non Patent Literatures 23 and 24). On the other hand, the general composition of a reaction buffer used in reverse transcription (First-Strand buffer (Life Technologies), PrimeScript Buffer (for cDNA synthesis) (TaKaRa), Maxima H Minus First Strand cDNA Synthesis RT-Buffer (Thermo Fisher), M-MuLV Reverse Transcriptase Reaction Buffer (New England Biolabs), AffinityScript RT Buffer (Agilent Biotechnology), etc.) comprises 50 mM Tris-HCl, 75 mM KCl, and 3 mM $MgCl_2$. Thus, the concentrations of Tris-HCl and KCl are high in such a reaction buffer used in reverse transcription. That is, it was predicted that the nuclease activity of DNase I on single-stranded DNA would be low under the conditions of the reverse transcription reaction buffer, and the RT-RamDA method would function. In reality, according to FRET analysis, nuclease activity was measured on the basis of 20 mM Tris-HCl, 50 mM KCl and 2 mM MgCl comprised in DNase I reaction buffer (Life Technologies), by increasing the concentrations of Tris-HCl and KCl. As a result, it was found that the nuclease activity of DNase I, not only on double-stranded DNA, but also on single-stranded DNA and DNA in an RNA-DNA hybrid, is significantly inhibited under conditions of high concentrations of Tris-HCl and KCl (FIG. 6). In the concentrations of Tris-HCl and KCl that were equivalent to those in a reverse transcription reaction buffer, the activity was suppressed to 43%, 16%, and 14%, in comparison to the conditions of a DNase I reaction buffer (FIG. 6, ##).

Next, the efficacy of the RT-RamDA method of using a non-specific DNA degrading enzyme, and in particular, the relationship between the salt concentration in the reaction solution and an amplification rate was examined. The salt concentration was changed from the composition of a DNase I reaction buffer to the composition of a reverse transcription reaction buffer, and whether the RT-RamDA method functions was examined using qPCR. As a result, unexpectedly, it was found that the RT-RamDA method provides sufficient amplification even under conditions of a DNase I reaction buffer having a high nuclease activity on single-stranded DNA (FIG. 7). Moreover, even if the concentrations of KCl and Tris-HCl were changed, it had only a small influence on the amplification rate (FIG. 7, a-i). On the other hand, it was found that the concentration of NaCl in the composition of a reverse transcription reaction buffer has a great influence on the amplification rate (FIG. 7, j-l). From these results, it is assumed that the composition of a reaction buffer containing no NaCl is desirable. Moreover, even in the case of using an in-house reaction buffer, the in-house reaction buffer exhibited an amplification rate that was not inferior to commercially available First-Strand buffer (Life Technologies) or PrimeScript Buffer (for Real Time) (TaKaRa) (FIG. 7, j, FS, and PS). From these results, it was found that the reaction buffer used in the RT-RamDA method is not limited to a certain reaction buffer, and further that the RT-RamDA method functions non-dependently on a salt-concentration-dependent nuclease activity. From these findings, it was suggested that factors other than the salt concentration in the reaction buffer should suppress the decomposition of cDNA.

Contribution of T4 Gene 32 Protein to Protection of cDNA and Stabilization of Amplification It has been reported that the T4 gene 32 protein has an action to bind to single-stranded DNA, so as to protect the single-stranded DNA from nuclease (Non Patent Literature 25). Thus, the fragmentation state of cDNA according to the RT-RamDA method of using, as a template, poly-A-added artificially synthesized RNA, and also using only an oligo dT primer, was examined based on the presence or absence of a T4 gene 32 protein (FIG. 8). As a result, it was found from the electrophoretic patterns that, in both cases of DNase I and dsDNase, the fragmentation of cDNA is suppressed by combining the enzyme with a T4 gene 32 protein, rather than in the case of using DNase alone (FIG. 8, A). In the analysis using BioAnalyzer, not only similar results could be obtained, but it was also found that the yield of cDNA was increased to nearly 10 times by allowing DNase to act thereon (FIG. 8, B). It is considered that these results suggest global amplification of cDNA by a strand displacement reaction. Subsequently, using qPCR, the amplification rate from the 3'-end to the 5'-end in template RNA was examined (FIG. 9). As a result, in the case of using DNase I alone, almost no amplification was observed. In contrast, when DNase I was combined with a T4 gene 32 protein, amplification was observed at a magnification of nearly 10 times (FIGS. 9A and 9B). Furthermore, it was found that the amplification rate on the 3' side was improved in comparison to dsDNase (FIG. 9,A). On the other hand, in the case of dsDNase, since dsDNase does not originally have a degradation activity on single-stranded DNA, it exhibited a high amplification rate, even when it was allowed to act alone. However, dsDNase resulted in a large fluctuation in the amplification rates on single RNA (FIGS. 9A and 9C). Since these conditions were almost equivalent to the conditions of RamDA-B, it was suggested that a fluctuation in the amplification, not only among genes, but also within a single gene, should be increased, unless there is a T4 gene 32 protein. From these results, it was suggested that, in RamDA-D of using DNase I, the T4 gene 32 protein should have two roles for contributing suppression of the decomposition of cDNA and stabilization of the amplification rate among genes or within a single gene.

T4 Gene 32 Protein Having Action to Improve Ratio Between Nuclease Activity on DNA in RNA-DNA Hybrid Strand and Activity on Single-Stranded DNA For the function of the RT-RamDA method of using DNase I, it is considered important that the decomposed amount of amplified DNA is smaller than the amount of strand displacement amplification caused by formation of a nick in an RNA-cDNA strand, namely, that nuclease activity on single-stranded DNA is sufficiently smaller than activity on DNA in an RNA-DNA hybrid strand. From an experiment regarding fragmentation of cDNA and amplification rate (FIGS. 8 and 9), the T4 gene 32 protein was assumed to contribute thereto. Hence, according to FRET analysis, the action of the T4 gene 32 protein on nuclease activity in a reverse transcription reaction buffer was examined (FIG. 10). As a result, it was found that the activity on the single-stranded DNA was reduced to 25% by adding the T4 gene 32 protein into the reverse transcription reaction buffer. In contrast, there was almost no fluctuation in the activity on double-stranded DNA, and the activity on DNA in the RNA-DNA hybrid strand was approximately 60% (FIG. 10, A). Subsequently, the ratio of the activity on single-stranded DNA to the nuclease activity on DNA in an RNA-DNA hybrid strand was examined. As a result, it was found that the activity ratio was improved from 40% to 14% by addition of the T4 gene 32 protein (FIG. 10, B). This improvement of the ratio is assumed to be a key factor for the efficacy of the RT-RamDA method. On the other hand, in the case of dsDNase, the activity ratio was merely approximately 7% even in the absence of the T4 gene 32 protein, and thus, it is considered that RamDA-B and RamDA-C without using T4 gene 32 proteins sufficiently function (FIG. 10, B).

RamDA-D Showing Reaction Time-Dependent Amplification Rate

Whether the amplification rate would be improved in a reaction time-dependent manner was examined using a 1-cell lysate of mouse ES cells as a template (FIG. 11). A relative value of the yield of cDNA was measured by qPCR. As a result, it was found that as the reaction time at 37° C. was increased to 30, 60, and 120 minutes, the yield was also increased to approximately 10, 20, and 30 times, respectively (FIG. 11). Such a phenomenon was not observed in RamDA-A of using dsDNase (the data is not shown). The nuclease activity of dsDNase was significantly inhibited in a reverse transcription reaction buffer, in particular, in the presence of a T4 gene 32 protein, and the nuclease activity of dsDNase on DNA in an RNA-DNA hybrid was only about 6%, in comparison to the nuclease activity of DNase I (FIG. 10, A). This may cause a difference in the amplification rate between the use of DNase I and the use of dsDNase. On the other hand, it was confirmed that RamDA-D functions without problems even in a crude sample containing impurities, such as a cell lysate. Moreover, with regard to the nuclease activity on double-stranded DNA in a reverse transcription reaction, the activity of DNase I was higher than the activity of dsDNase, and thus, it was suggested that RamDA-D should be effective regarding not only an amplification rate, but also an ability to remove contamination (FIG. 10, A).

RamDA-D that is not Limited to Specific RNase H Minus Reverse Transcriptase, and in Addition, Functions Also on RNA Corresponding to 100 Cells.

In order to confirm whether RamDA-D is limited to a specific RNase H minus reverse transcriptase, an examination was carried out using reverse transcriptase of SuperScript series (Life Technologies), as well as PrimeScript RT Enzyme Mix I (FIG. 12). As a result, amplification of cDNA could be confirmed in SuperScript II and III. Among others, SuperScript II exhibited an amplification rate that was equivalent to that of PrimeScript RT Enzyme Mix I (FIG. 12, SSII). Furthermore, it was confirmed that RamDA-D functions even in the case of using Maxima H Minus First Strand cDNA Synthesis Kit (Thermo Fisher) or ReverTra Ace qPCR RT Kit (TOYOBO) (the data is not shown). From these results, it was found that RamDA-D is not limited to a specific RNase H minus reverse transcriptase. Further, it was also found that RamDA-D functions without problems even in RNA in an amount greater than 10 pg of total RNA corresponding to a single cell, for example, in 200 pg of RNA or 1 ng of RNA (FIG. 12, 200 pg, 1 ng). From these results, it was suggested that sufficient amplification performance should be ensured even using template RNA in an amount of at least 100 cells.

As stated above, the RT-RamDA method can be an extremely useful means as a technique of amplifying trace RNA, and in particular, the amplification rate provided by RamDA-C should be an extremely great advantage in the analysis of detecting a specific target gene. On the other hand, since RamDA-C causes a large fluctuation in the amplification rates among genes, RamDA-A involving the use of a T4 gene 32 protein is effective for an analysis requiring uniform amplification. Moreover, RamDA-D involving the use of such a T4 gene 32 protein and DNase I as a non-specific DNA degrading enzyme has a high amplification rate and also has a small amplification fluctuation among genes or within a single gene. Furthermore, since the nuclease activity of DNase I on double-stranded DNA during a reverse transcription reaction is also maintained at a level higher than that of a double strand-specific DNA degrading enzyme, it is expected that RamDA-D will have the effect of reducing the influence of DNA contamination. As described above, RamDA-D is a method comprising both the superiority of RamDA-A and that of RamDA-B, and this is an extremely effective and simple reverse transcription method targeting a trace amount of RNA.

The present application claims priority from Japanese Patent Application No. 2014-200258 (filed on Sep. 30, 2014); the disclosure of which is hereby incorporated by reference in its entirety. In addition, all patent publications, patent applications, and publications cited herein are incorporated herein by reference in their entirety.

The invention claimed is:

1. A method for amplifying a nucleic acid, comprising:
incubating a mixture comprising:
   template RNA,
   a primer,
   a degrading enzyme specific to DNA in a RNA-DNA hybrid,
   an RNase H minus reverse transcriptase, and
   a substrate,
synthesizing a complementary DNA (cDNA) of the template RNA by the RNA-dependent DNA polymerase activity of the RNase H minus reverse transcriptase, then randomly cleaving the cDNA strand in the hybrid strand of RNA and cDNA by the degrading enzyme specific to DNA in RNA-DNA hybrid, then separating the cDNA strand on the 3' side from the RNA by the strand displacement activity of the RNase H minus reverse transcriptase, while using the cleavage site as a starting point, and then synthesizing a new cDNA in a portion separated by the RNase H minus reverse transcriptase to amplify cDNA in a reverse transcription reaction, wherein the degrading enzyme specific to DNA in the RNA-DNA hybrid has an activity of cleaving a DNA strand in the RNA-DNA hybrid.

2. The method for amplifying a nucleic acid according to claim 1, wherein
the mixture comprises a double strand-specific DNA degrading enzyme as a degrading enzyme specific to DNA in RNA-DNA hybrid, and
the double strand-specific DNA degrading enzyme has an activity of cleaving the DNA strand in the RNA-DNA hybrid, and substantially does not have an activity of cleaving the RNA strand in the RNA-DNA hybrid, single-stranded DNA and single-stranded RNA.

3. The method for amplifying a nucleic acid according to claim 1, wherein
the mixture comprises a non-specific DNA degrading enzyme as a degrading enzyme specific to DNA in RNA-DNA hybrid, and the non-specific DNA degrading enzyme has an activity of cleaving the DNA strand in the RNA-DNA hybrid, and substantially does not have an activity of cleaving the RNA strand in the RNA-DNA hybrid, and single-stranded RNA.

4. The method for amplifying a nucleic acid according to claim 1, wherein the degrading enzyme specific to DNA in RNA-DNA hybrid has a DNA-degrading activity even at a temperature of lower than 60° C.

5. The method for amplifying a nucleic acid according to claim 2, wherein the double strand-specific DNA degrading enzyme is a double strand-specific DNA degrading enzyme derived from Crustacea, or a variant thereof.

6. The method for amplifying a nucleic acid according to claim 5, wherein the double strand-specific DNA degrading enzyme is a double strand-specific DNA degrading enzyme derived from a shrimp, or a variant thereof.

7. The method for amplifying a nucleic acid according to claim 3, wherein the non-specific DNA degrading enzyme is a non-specific DNA degrading enzyme derived from a mammal, or a variant thereof.

8. The method for amplifying a nucleic acid according to claim 7, wherein the non-specific DNA degrading enzyme is a non-specific DNA degrading enzyme derived from a bovine, or a variant thereof.

9. The method for amplifying a nucleic acid according to claim 1, wherein the primer is one or more of a random primer, an oligo dT primer and a sequence-specific primer.

10. The method for amplifying a nucleic acid according to claim 1, wherein the primer is modified with a cation unit so that a Tm value of the primer is increased.

11. The method for amplifying a nucleic acid according to claim 1, wherein the primer is a Zip Nucleic Acid (ZNA) primer.

12. The method for amplifying a nucleic acid according to claim 1, wherein the mixture further comprises a single-stranded DNA-binding protein.

13. The method for amplifying a nucleic acid according to claim 1, wherein the template RNA is trace RNA corresponding to a volume ranging from a single cell to several hundreds of cells.

* * * * *

SEQUENCE LISTING

<160> NUMBER OF SEQ ID NOS: 80

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
cgccatcgga ggttc                                                    15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
gaacctccga tggcg                                                    15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
cgccatcgga ggttc                                              15

<210> SEQ ID NO 4
<211> LENGTH: 15
<212> TYPE: RNA
<213> ORGANISM: Artificial Sequence
<220> FEATURE:
<223> OTHER INFORMATION: Description of Artificial Sequence: Synthetic
      RNA

<400> SEQUENCE: 4
gaaccuccga uggcg                                              15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
gaacctccga tggcg                                              15

<210> SEQ ID NO 6
<211> LENGTH: 15
<212> TYPE: RNA
<213> ORGANISM: Artificial Sequence
<220> FEATURE:
<223> OTHER INFORMATION: Description of Artificial Sequence: Synthetic
      RNA

<400> SEQUENCE: 6
gaaccuccga uggcg                                              15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
cgccatcgga ggttc                                              15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
gaacctccga tggcg                                              15

-continued

```
<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
cgccatcgga ggttc                                                     15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
gaacctccga tggcg                                                     15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
cgccatcgga ggttc                                                     15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
gaacctccga tggcg                                                     15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
cgccatcgga ggttc                                                     15

<210> SEQ ID NO 14
<211> LENGTH: 15
<212> TYPE: RNA
<213> ORGANISM: Artificial Sequence
<220> FEATURE:
<223> OTHER INFORMATION: Description of Artificial Sequence: Synthetic
      RNA

<400> SEQUENCE: 14
gaaccuccga uggcg                                                     15

<210> SEQ ID NO 15
```

<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
cgccatcgga ggttc                                                        15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
cgccatcgga ggttc                                                        15

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
tgaccagaga tgagaccaac tatgg                                             25

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
aagtgggagt gacctctcag agc                                               23

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
tgattcttct accagtccca aacaa                                             25

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
tgagagaaca cagtccgcat ctt                                               23

<210> SEQ ID NO 21
<211> LENGTH: 20

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
cccggaagag aaagcgaact                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
cgggcacttc agaaacatgg                                                    20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
tcttgctggg ttttgattct gc                                                 22

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
caaatccgaa taaactcctt ccttg                                              25

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
ctcaagccgg gtgcaaga                                                      18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
gcccgtggac aagcatgt                                                      18

<210> SEQ ID NO 27
<211> LENGTH: 18
<212> TYPE: DNA
```

<213> ORGANISM: Artificial Sequence
<220> FEATURE:
<223> OTHER INFORMATION: Description of Artificial Sequence: Synthetic
      DNA

<400> SEQUENCE: 27
ccttcgccat gggattcg                                                    18

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
cgccaggtaa tcgttgagca                                                  20

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
gtaccctcct tccaccggg                                                   19

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
gccattgctg aggtcacaca g                                                21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
cagtctgaga ccggcccag                                                   19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
tgtgcacgat ttccctcatg                                                  20

<210> SEQ ID NO 33
<211> LENGTH: 21
<212> TYPE: DNA
<213> ORGANISM: Artificial Sequence

```
<220> FEATURE:
<223> OTHER INFORMATION: Description of Artificial Sequence: Synthetic
      DNA

<400> SEQUENCE: 33
aaattagtca ttgcgggacc g                                              21

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
tcgttctgcc aatttaacag cttc                                           24

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
gaacaccaca ttttgacctt gtagg                                          25

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
gaaagcatct gactcaacag gca                                            23

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
gattgattta acaacgcccg aa                                             22

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
tccgtgctct aatgcaattt ttg                                            23

<210> SEQ ID NO 39
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      DNA

<400> SEQUENCE: 39
gaaaagcagc aaggacatcc g                                                   21

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
tgctccgctc ctcttgctc                                                      19

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
gtcaggcgtt aaactgtcag tcg                                                 23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
tttatccccc cgtctaatca atg                                                 23

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
tttcaatccg gcccttttagg                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
agtgcattgg cagcgatcag                                                     20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
```

DNA

<400> SEQUENCE: 45
actgcggaaa ttcttgtgcg                                                 20

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
cgaagaaggt cacggaattc g                                               21

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
ttttggcgcc cacagtgat                                                  19

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 48
gacaaacttc gctattgtgc cg                                              22

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 49
agctgaagca gcccgcata                                                  19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 50
gcggtctgga agcgttagc                                                  19

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 51
aatgcggctg cactggtg                                                            18

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 52
cgtctttata tttatggatt ccggc                                                    25

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 53
ttccgtttct actcctctga cgaa                                                     24

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 54
ggcatactcc acgcccg                                                             17

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 55
taaagaagcg ggcgtggagt a                                                        21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 56
tttggatcct cagcatccgt t                                                        21

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

```
<400> SEQUENCE: 57
ctcgagatgt ggaaaggact tatcc                                          25

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 58
catgtaaagt tagcgccggt gt                                             22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59
aatggttatg gctgtggcaa ag                                             22

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 60
cagcagcgga agtgttacct g                                              21

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
aattgtccgt tccatctgtg aga                                            23

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
gtaagggttg actgagttga caagg                                          25

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 63
```

```
gaaaaacggc acaggccttc                                              20

<210> SEQ ID NO 64
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 64
cgattgccgc cgcac                                                   15

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 65
ctgaaagatc cgaacacagc g                                            21

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
tcagtcggca atgtgacagg                                              20

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 67
agctgaccgt ctttgaaagc g                                            21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 68
ttccggcgac tgtttctgtt t                                            21

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
```
agtggctaaa cggaccgca                                          19

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 70
caccttcaca tggacaggag g                                       21

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 71
atgctggcgc ttctctcgt                                          19

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
tgggtctcgt catcctcatg                                         20

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 73
ctcgtcggcg gacttgtg                                           18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74
ggacgcggat catttggg                                           18

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75
gtgctgacaa gagacgcgag a                                       21

```
<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 76
tttacggcat cggcatatgg                                                   20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 77
atgttccatc agccgtaccg                                                   20

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 78
ggcgacgtgc tctacttttg a                                                 21

<210> SEQ ID NO 79
<211> LENGTH: 16
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 79
cggagcaggc ccaacg                                                       16

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 80
gggaaatgaa gcgcgagc                                                     18
```